US010537597B2

United States Patent
O'Mahony et al.

(10) Patent No.: US 10,537,597 B2
(45) Date of Patent: Jan. 21, 2020

(54) **USE OF *AKKERMANSIA MUCINIPHILA* FOR TREATING INFLAMMATORY CONDITIONS**

(71) Applicant: SCHWEIZERISCHES FORSCHUNGSINSTITUT FUR HOCHGEBRIGSKLIMA UND MEDIZIN IN DAVOS, Davos Platz (CH)

(72) Inventors: Liam O'Mahony, Davos Platz (CH); Cezmi A. Akdis, Davos Platz (CH); David Michalovich, Stevenage Hertfordshire (GB); Edith M. Hessel, Stevenage Hertfordshire (GB); James R. Brown, Collegeville, PA (US); David N. Mayhew, King of Prussia, PA (US); Sorif Uddin, Stevenage Hertfordshire (GB)

(73) Assignee: Schweizerisches Forschungsinstitut Fur Hochgebrigsklima Und Medizin In Davos, Davos Platz (CH)

( * ) Notice: Subject to any disclaimer, the term of this patent is extended or adjusted under 35 U.S.C. 154(b) by 0 days.

(21) Appl. No.: 15/766,215

(22) PCT Filed: Oct. 5, 2016

(86) PCT No.: PCT/GB2016/053097
§ 371 (c)(1),
(2) Date: Apr. 5, 2018

(87) PCT Pub. No.: WO2017/060698
PCT Pub. Date: Apr. 13, 2017

(65) Prior Publication Data
US 2018/0296613 A1  Oct. 18, 2018

Related U.S. Application Data

(60) Provisional application No. 62/237,131, filed on Oct. 5, 2015.

(51) Int. Cl.
| | |
|---|---|
| *A61K 9/00* | (2006.01) |
| *A61K 35/741* | (2015.01) |
| *A61P 29/00* | (2006.01) |
| *A61K 35/74* | (2015.01) |

(52) U.S. Cl.
CPC .......... *A61K 35/741* (2013.01); *A61K 9/0053* (2013.01); *A61K 35/74* (2013.01); *A61P 29/00* (2018.01)

(58) Field of Classification Search
None
See application file for complete search history.

(56) References Cited

FOREIGN PATENT DOCUMENTS

| WO | 2014/075745 A1 | 5/2014 |
| WO | 2014/076246 A1 | 5/2014 |
| WO | 2014/201037 A2 | 12/2014 |

OTHER PUBLICATIONS

Belzer et al., "Microbes inside-from diversity to function: the case of Akkermansia", ISME J. 6:1449-1458 (2012).
Brown, "Akkermansia: new discoveries from the microbiome", Functional Medicine (2014).
Candela et al., "Unbalance of intestinal microbiota in atopic children", BMC Microbiol. 12:95 (2012).
Derrien et al., "Modulation of Mucosal Immune Response, Tolerance, and Proliferation in Mice Colonized by the Mucin-Degrader Akkermansia muciniphila", Front. Microbiol. 2:166 (2011).
Drell et al., "Differences in Gut Microbiota Between Atopic and Healthy Children", Curr. Microbiol. 71:177-183 (2015).
Ganesh et al., "Commensal Akkermansia muciniphila exacerbates gut inflammation in *Salmonella typhimurium*-infected gnotobiotic mice", PLoS One 8(9):e74963 (2013).
Gibson et al., "Inulin and Oligofructose: New Scientific Developments", Nutrition Today 43(2):54-59 (2008).
Huang et al., "The Microbiome and Asthma", AnnalsATS 11(Suppl. 1):S48-S51 (2014).
Png et al., "Mucolytic bacteria with increased prevalence in IBD mucosa augment in vitro utilization of mucin by other bacteria", Am. J. Gastroenterol. 105:2420-2428 (2010).
Schneeberger et al., "Akkermansia muciniphila inversely correlates with the onset of inflammation, altered adipose tissue metabolism and metabolic disorders during obesity in mice", Sci. Rep. 5:16643 (2015).

*Primary Examiner* — Padmavathi Baskar
(74) *Attorney, Agent, or Firm* — Nixon Peabody LLP; Mark J. FitzGerald; Teresa A. Ptashka

(57) ABSTRACT

The invention relates to use of *Akkermansia muciniphila*, a mucin-degrading bacterial species found in the human gut, for treating undesirable inflammatory activity not caused by any metabolic disorder and/or obesity, especially for example undesirable airway inflammatory activity as seen with asthma.

15 Claims, 21 Drawing Sheets
Specification includes a Sequence Listing.

(i)

(ii)

(iii)

USE OF *AKKERMANSIA MUCINIPHILA* FOR TREATING INFLAMMATORY CONDITIONS

CROSS-REFERENCE TO RELATED APPLICATIONS

This application is a 35 U.S.C. § 371 National Phase Entry Application of International Application No. PCT/GB2016/053097, filed Oct. 5, 2016, which designates the U.S. and which claims priority to U.S. application Ser. No. 62/237,131, filed Oct. 5, 2015, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 5, 2018, is named P224214US_WO_ST25_3429641.txt and is 858 bytes in size.

FIELD OF THE INVENTION

The invention relates to the use of *Akkermansia muciniphila* as an immunomodulatory biotherapeutic agent for treating asthma. More generally, it relates to use of *Akkermansia muciniphila*, a mucin-degrading bacterial species found in the human gut, for treating undesirable inflammatory activity unrelated to any metabolic disorder and or obesity. In this context, "unrelated to" will be understood to mean "not caused by". Of especial interest is use of *Akkermansia muciniphila* in the prophylaxis and/or treatment of airway inflammation in asthmatic patients identified as having a lower level of that microbe in the gut compared to healthy individuals. Commonly such asthmatics can be expected to have asthma which can be categorized as severe.

BACKGROUND TO THE INVENTION

The human microbiome is a microbial community, which can be described as the sum of all microbial life living in or on specific sites of the human body. Recent advances in DNA sequencing techniques have facilitated more in-depth analysis of the microbiomes of the gut, skin, genito-urinary tract and the lung, revealing a microbial super organ residing symbiotically with host mucosal surfaces. It is becoming better appreciated that the composition and activity of the microbiome has significant metabolic, nutritional and immunological effects on the host (1). The microbiome evolves within a host from birth, constantly being fine-tuned to maintain a homeostatic balance with the host's immune system. This evolution is influenced by host factors, such as the adaptive and innate immune responses, external factors such as diet, medication and toxin exposure, and illness.

The gastrointestinal tract has the greatest number and diversity of microbes, with approximately 100 trillion microbes residing in the gut (2 to 10 times the total number of human cells in the entire body), while the collective genomes of the gut microbiome contain approximately 100 times more genes than the human genome. These microbes are highly adapted to survive within complex community structures, requiring nutrients from other microbes and/or host processes. Interestingly, using sequencing approaches, over 1,000 different bacterial species have been identified within the gut microbiome. However, a specific individual's microbiome typically contains only 300-500 different species, leading to enormous inter-individual variability in microbiome composition. This variability is even more pronounced when patients with diseases, such as inflammatory bowel disease, are compared to healthy individuals, supporting the concept that an imbalance of certain microbes (i.e. dysbiosis) within the microbiome may contribute to aberrant inflammatory and metabolic responses (2). Similarly, alterations in the microbiome of the lung have been associated with lung-associated disorders such as asthma and chronic obstructive pulmonary disease (3).

The microbiome supports the development of epithelial barrier function and integrity, while promoting potent tolerance and protective immune mechanisms within mucosal tissues (4). Microbes have direct effects on host immune responses and metabolites derived from microbial fermentation of nutrients within the gut not only contribute to host energy intake, but also significantly influence host immunological responses (e.g. short-chain fatty acids and histamine) (5, 6). Appropriate cellular and molecular networks involve innate pattern recognition receptor activation, T and B cell polarization and expansion, secretion of a wide range of effector and regulatory cytokines and host metabolites. Ultimately this trialogue between the microbiome, immune cells and tissue cells within the gut results in the establishment of optimal digestive capabilities, gut motility, immune tolerance to foods and certain microbial antigens, and protection against pathogens.

The immunological consequences of bacterial processes within the gastrointestinal tract have effects on organs distant to the gut itself (7). For example, respiratory inflammation has been treated in murine models by oral administration of certain probiotic bacteria such as Lactobacilli and Bifidobacteria (8, 9). In addition, a reduced gut bacterial diversity early in life increases the risk of later life asthma (10).

*Akkermansia* species are commensal microorganisms. They have been isolated from the microbial flora within the human gastrointestinal tract (11). The immune system within the gastrointestinal tract cannot have a pronounced reaction to members of this flora, as the resulting inflammatory activity would also destroy host cells and tissue function. Therefore, some mechanism(s) exist whereby the immune system can recognize commensal non-pathogenic members of the gastrointestinal flora as being different to pathogenic organisms.

This ensures that damage to host tissues is restricted and a defensive barrier is still maintained. *Akkermansia muciniphila* has been shown in a murine model to modulate pathways involved in establishing homeostasis for basal metabolism and immune tolerance toward commensal microbiota (12).

*Akkermansia muciniphila* has been previously reported to be reduced in faecal samples from obese individuals and patients with inflammatory bowel disease (13). *Akkermansia muciniphila* is associated with a healthier metabolic status and better clinical outcomes after a calorie restriction intervention in overweight/obese adults (14). Indeed, published International Patent Application WO 2014/075745, and published International Application WO 2014/076246 claiming priority therefrom, concern the protective effects of *Akkermansia muciniphila* in obese individuals and propose administration of *Akkermansia muciniphila* to individuals exhibiting obesity and/or metabolic disorders such as type 2 diabetes to provide various beneficial effects (15). Administration of *Akkermansia muciniphilia* to obese and type 2 diabetic mice has been shown to correlate with an improved metabolic profile and to be able to protect against high fat diet-induced metabolic disorders. Beneficial effects were reported of interest in relation to associated gut inflammation including increase of intestinal levels of endocannabinoids (16). However such studies provide no information relevant to ameliorating other forms of inflammation, including gut inflammation of different etiology.

It has now been discovered that *Akkermansia muciniphila* levels are decreased in non-obese asthma patients with uncontrolled symptoms and this bacterium is protective in non-obese animal models of respiratory inflammation. It has been previously described that the same bacterium exerts immunoregulatory effects within the gastrointestinal tract, possibly directly and indirectly via the digestion of intestinal mucins and subsequent effects on SCFA secretion by the microbiome (see again 12). Lower prevalence of *Akkermansia muciniphila* has also previously been correlated with IgE-mediated atopic disease in a small number of allergic children (17). However those studies provide no more than a mere correlation and provide no foundation for extrapolation of any beneficial effect of oral administration of the same microbe at a site remote from the gastrointestinal (GI) tract, nor evidence of a route by which this might be achieved.

SUMMARY OF THE INVENTION

Studies reported herein for the first time show linkage in humans between decreased gastrointestinal levels of *Akkermansia muciniphila* and the severity of a respiratory disease, more particularly asthma, with demonstration of protective effects in therapeutically relevant murine models of respiratory inflammation. Furthermore, it has been shown that *Akkermansia muciniphila* can induce ILT4 (immunoglobulin-like transcript 4) expression on human monocyte-derived dendritic cells (MDDCs). ILT4 (also sometimes referred to as LILRB2) is known to be important for inducing regulatory T cells which can secrete IL-10, an anti-inflammatory cytokine. Moreover, mice administered *Akkermansia muciniphila* have been found to have increased regulatory T cells that secrete IL-10 amongst lung tissue lymphocytes. These observations, as described more fully below, provide for the first time foundation for probiotic use of *Akkermansia muciniphila* strains for the prophylaxis and/or treatment of respiratory inflammation, e.g. as associated with asthma, especially severe asthma, and other undesirable inflammation independent from and unconnected with any metabolic disorder and/or obesity.

It will be understood that the metabolic disorders referred to above are related to a disorder of energy utilization and storage. A common sign of metabolic disorder is central obesity or overweight with adipose tissue accumulation particularly around the waist and trunk. Other signs of metabolic disorder include high blood pressure, decreased fasting serum HDL cholesterol, elevated fasting serum triglyceride level (VLDL triglyceride), impaired fasting glucose, insulin resistance, or prediabetes. Associated conditions include hyperuricemia, fatty liver (especially in concurrent obesity) progressing to nonalcoholic fatty liver disease, polycystic ovarian syndrome (in women), erectile dysfunction (in men), and acanthosis nigricans.

Severe asthma as referred to herein can be understood and defined as follows: When a diagnosis of asthma is confirmed and comorbidities have been addressed, severe asthma is defined as "asthma which requires treatment with high dose inhaled corticosteroids (ICS) plus a second controller (and/ or systemic CS) to prevent it from becoming "uncontrolled" or which remains "uncontrolled" despite this therapy." (18)

In one aspect, the present invention thus provides a composition comprising one or more *Akkermansia muciniphila* strains for use in the prophylaxis and/or treatment of undesirable inflammatory activity wherein said inflammatory activity is not caused by a metabolic disorder and/or obesity.

Such a composition may be a probiotic composition for delivery of the one or more *Akkermansia muciniphilia* strains in the GI tract, preferably for oral administration, e.g. in the form of a beverage or other form of nutritional composition for oral consumption. It may be in the form of a pharmaceutical composition for administration of one of more *Akkermansia muciniphila* strains in the GI tract, preferably by oral administration. The composition may be a strain-release composition which is not ingested in which case said use further comprises the pre-step of contacting said composition with a liquid whereby the one or more probiotic strains are released into the liquid and the resulting probiotic liquid composition is then ingested. It is envisaged that the probiotic composition employed may alternatively be formulated and packaged for aerosol delivery.

*Akkermansia muciniphila* strains for use in applying the invention will be understood to include naturally-occurring strains and additionally variants and genetically-modified mutants of naturally-occurring *Akkermansia muciniphila* strains, in any form, provided that desired immunomodulatory effect when in the gut is maintained.

Alternatively, the invention provides a method for the prophylaxis and/or treatment of undesirable inflammatory activity which comprises administration of one or more *Akkermansia muciniphila* strains to the GI tract, wherein said inflammatory activity is not caused by a metabolic disorder and/or obesity.

The invention will be further described below with reference the following figures.

Data presented as mean+/−SEM. Data analysed by one-way ANOVA with Tukey p value correction. Data log transformed where necessary to stabilize variance. P values of less than 0.05 were considered significant.

Figure 5A:
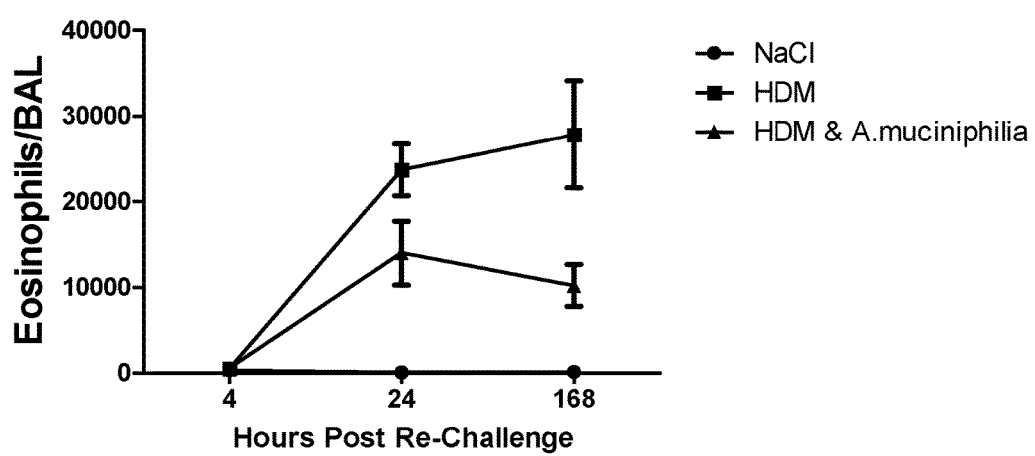
Figure 5B:
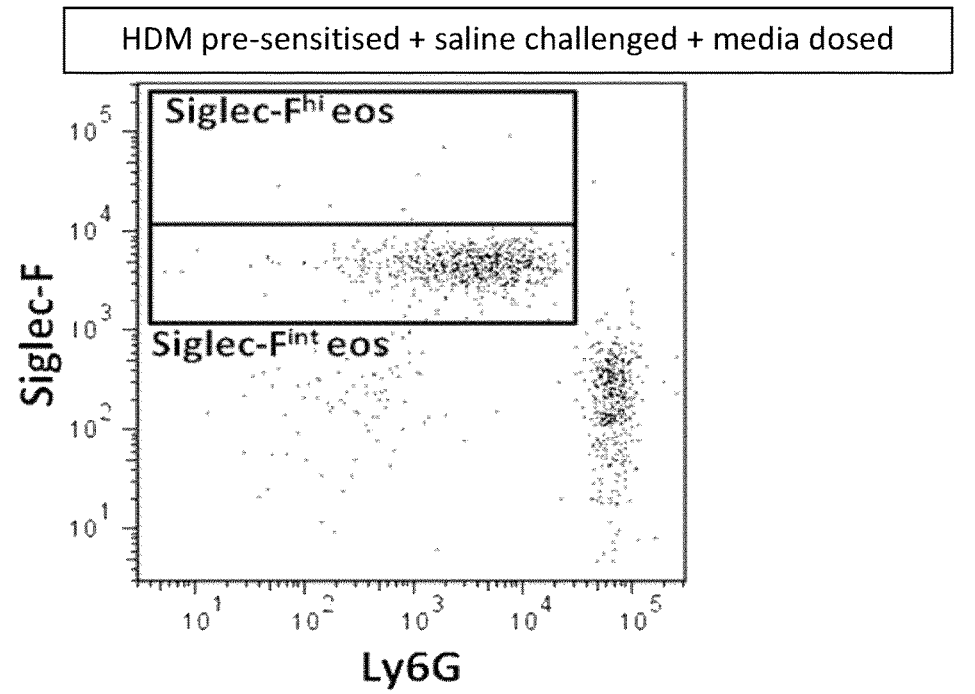
Figure 5B:
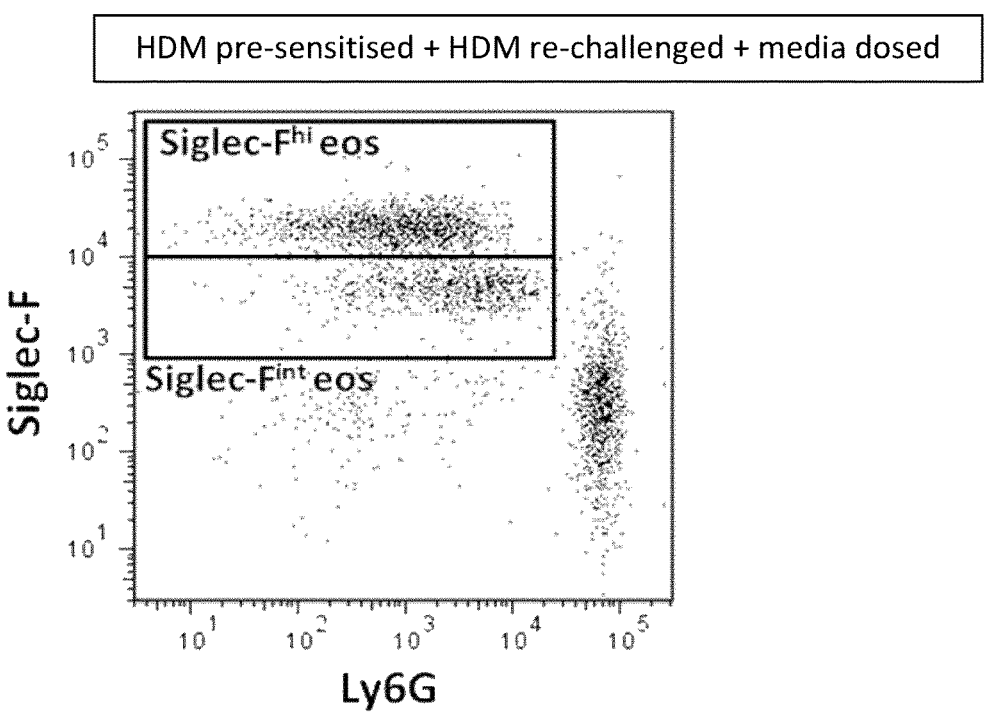
Figure 5B:
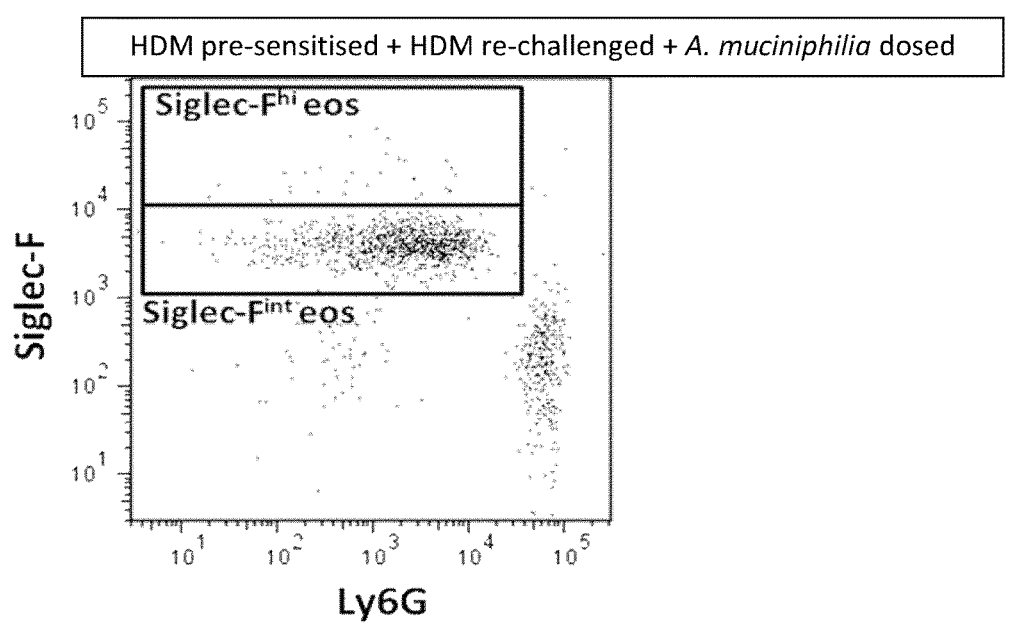
Figure 5C:
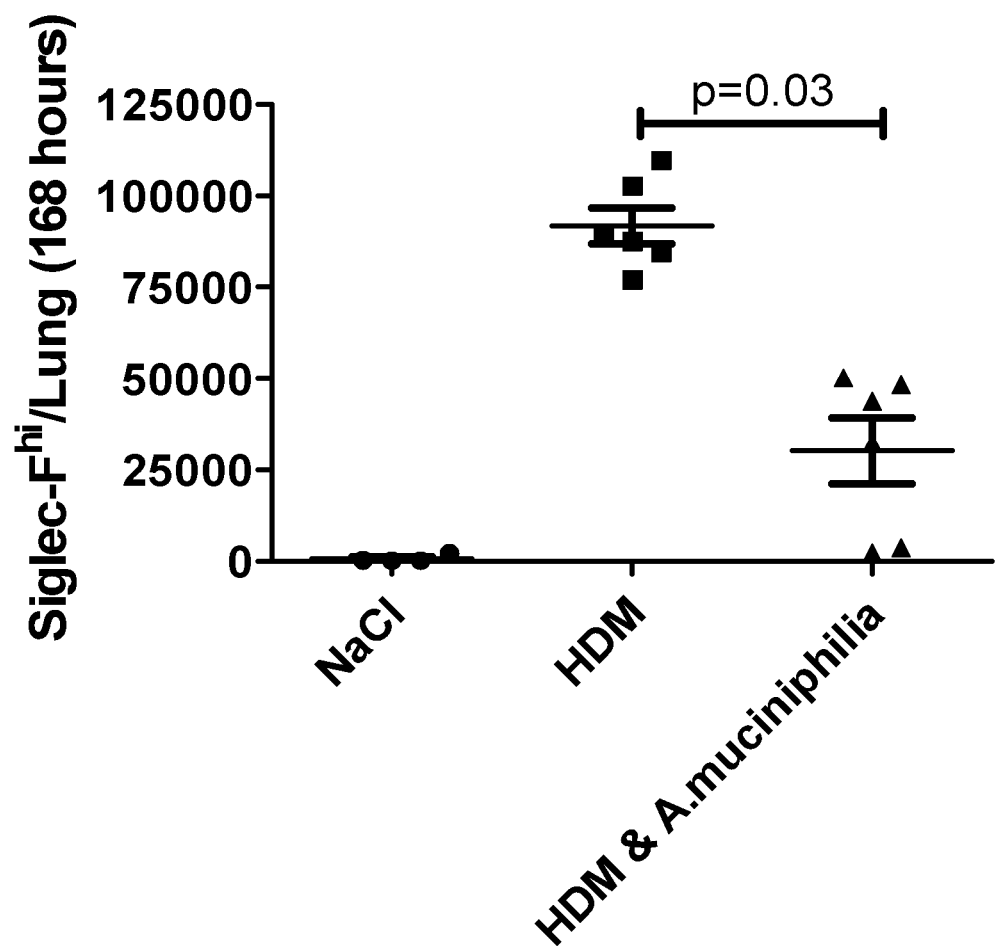

FIG. 5A illustrates the suppressive effect of *Akkermansia muciniphila* feeding on eosinophil recruitment to the lungs following re-challenge with house dust mite extract in the chronic house dust mite challenge model, with FIGS. 5B and C highlighting the decrease in Siglec-$F^{high}$ eosinophils in the lung tissue.

Figure 6:
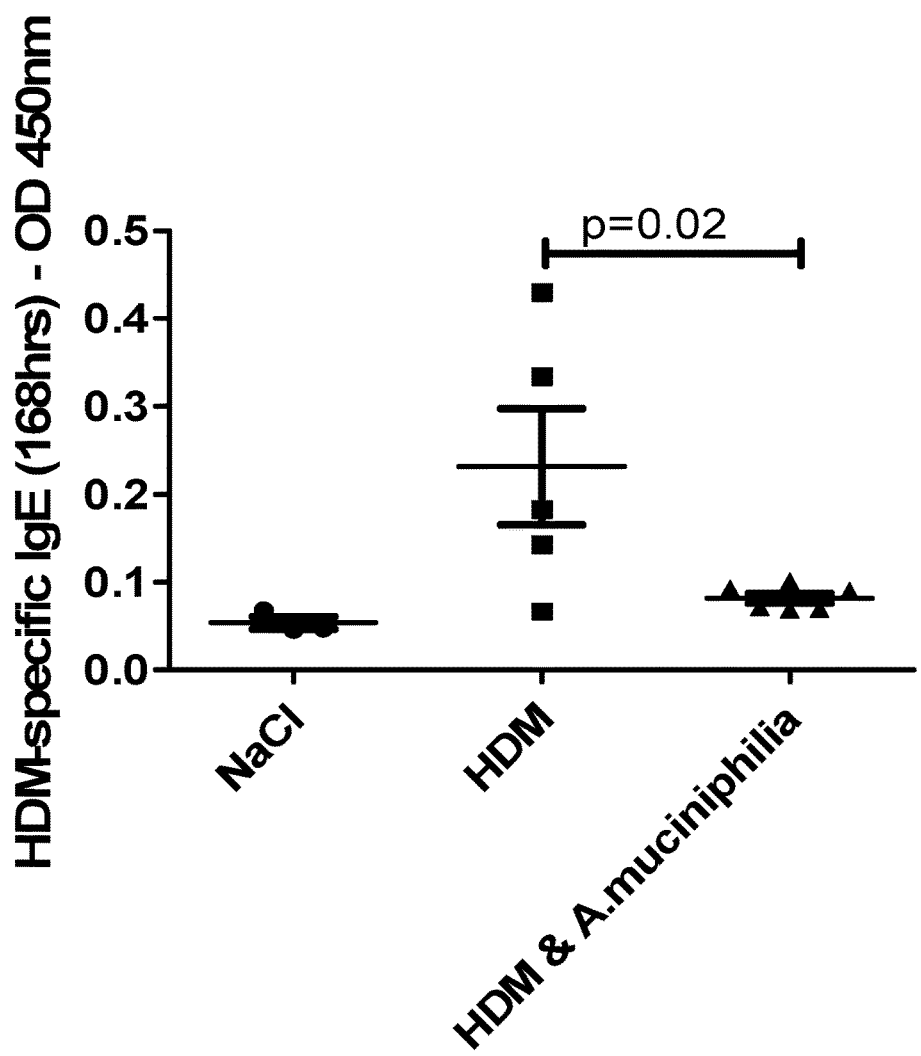

FIG. 6 illustrates the suppressive effect of *Akkermansia muciniphila* feeding on IgE production, specific to house dust mite extract, following re-challenge with house dust mite extract in the chronic house dust mite challenge model.

Figure 7A:
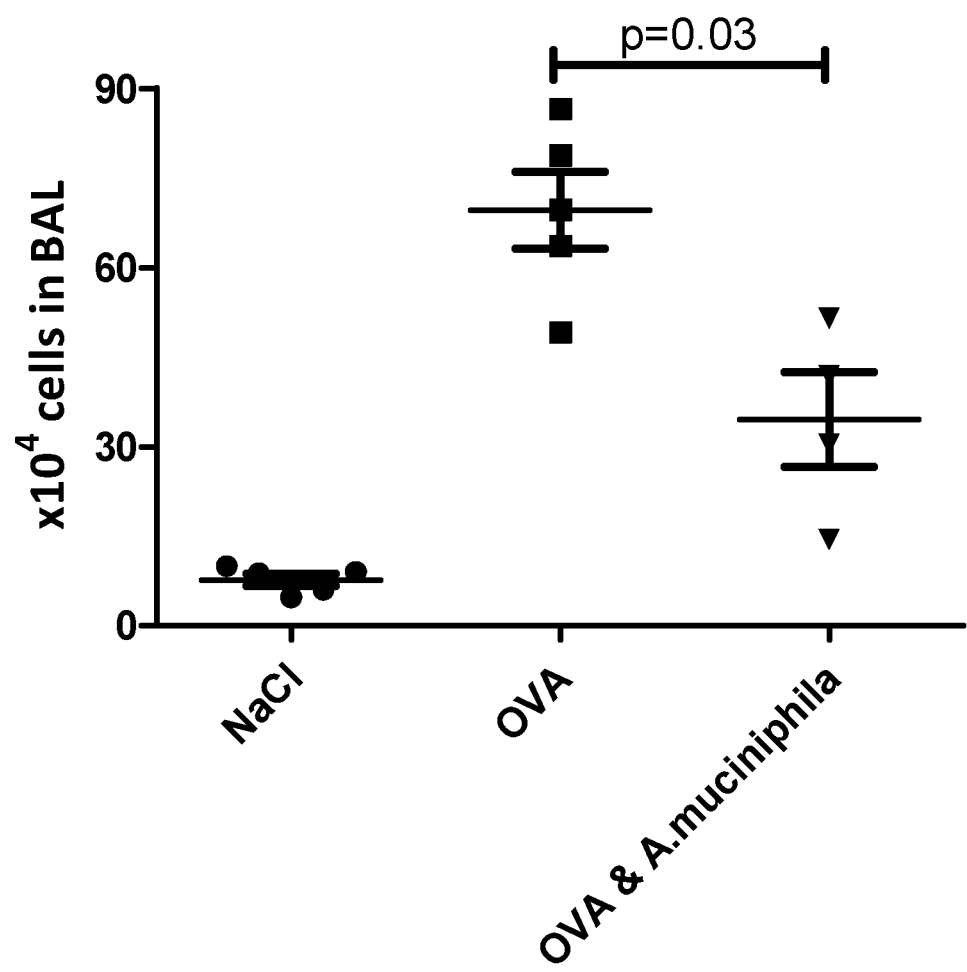
Figure 7B:
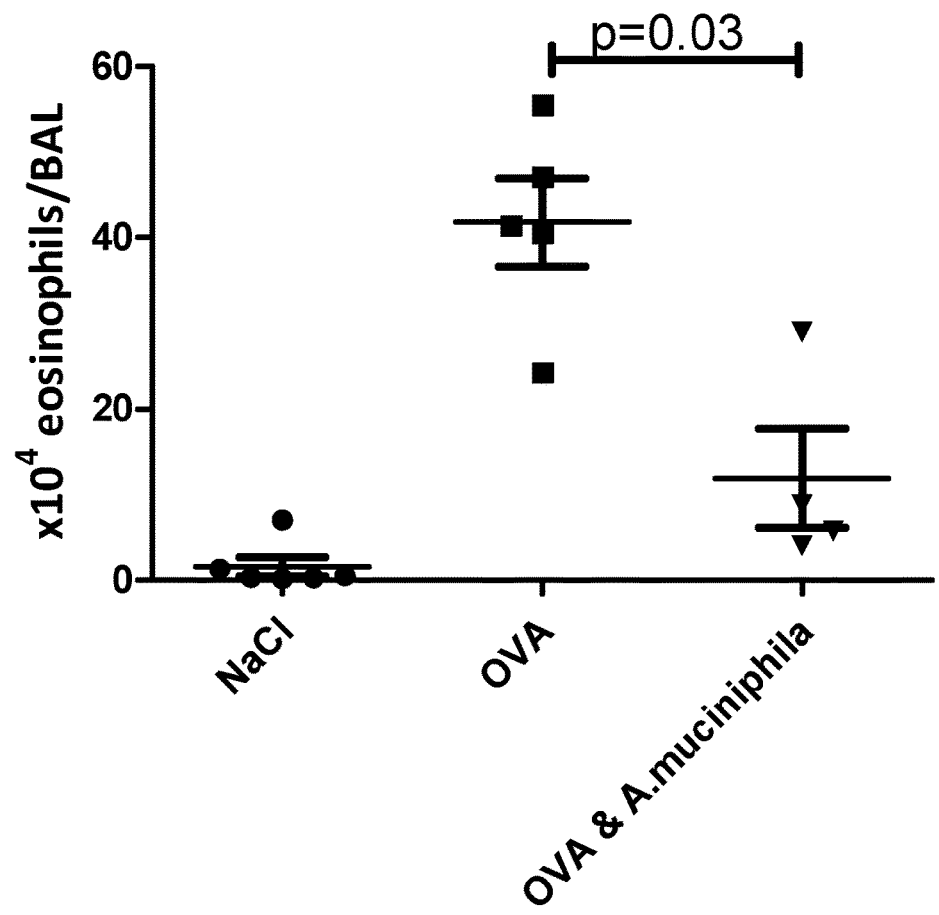

FIG. 7A is a graph showing the suppressive effect of *Akkermansia muciniphila* feeding on inflammatory cell recruitment to the lungs of ovalbumin (OVA) challenged mice, with FIG. 7B highlighting the decrease in inflammatory eosinophils.

Figure 8A:
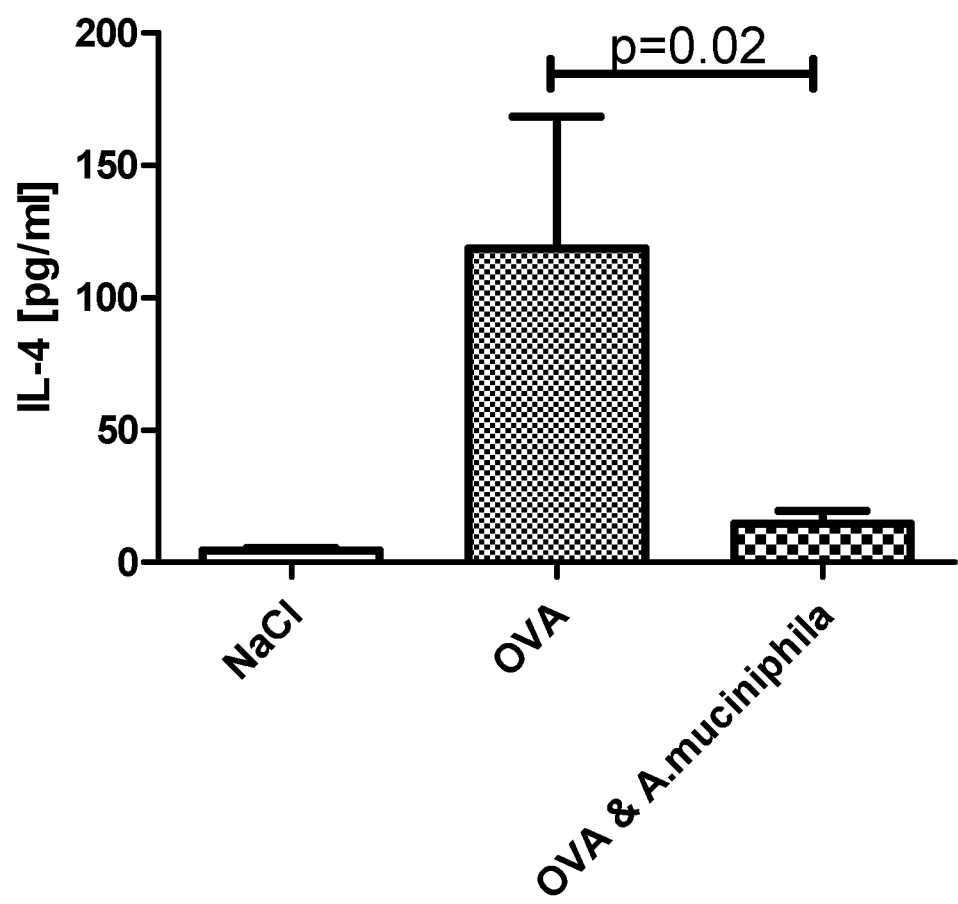
Figure 8B:
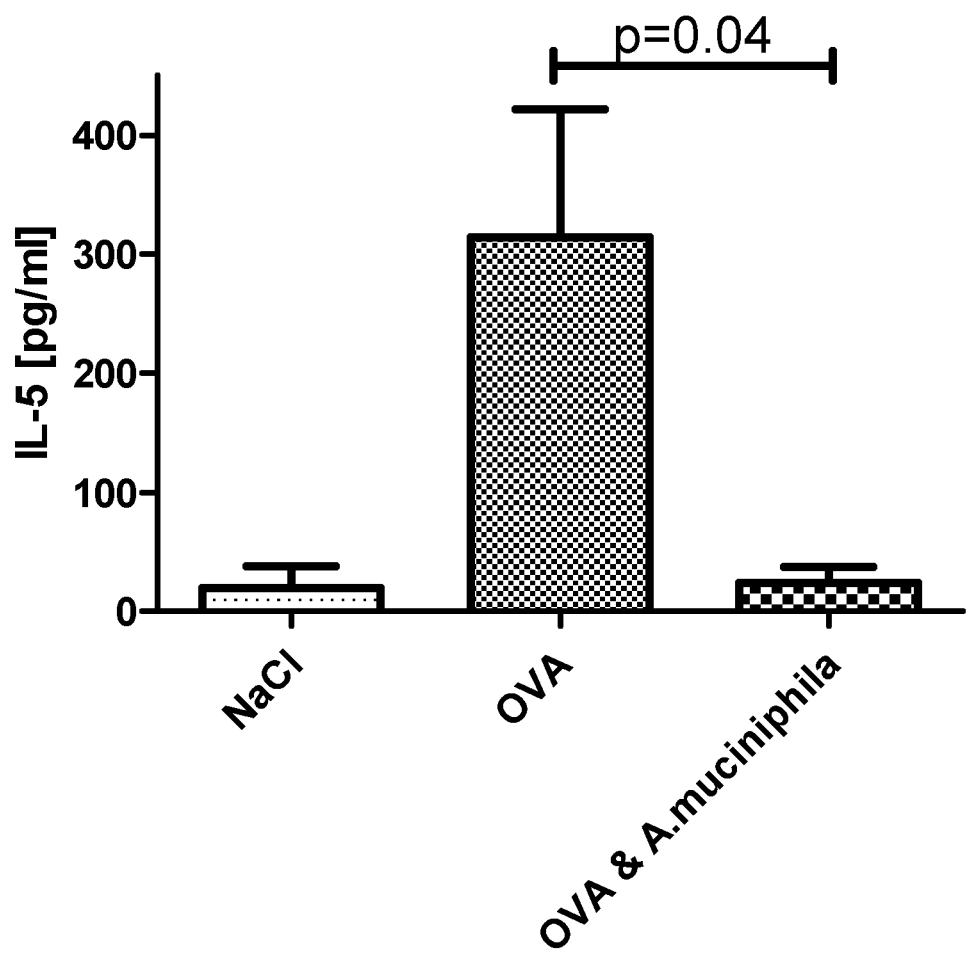

FIGS. 8A and 8B illustrate that cells within the lung tissue of *Akkermansia muciniphila* fed animals secrete significantly less interleukin (IL)-4 (FIG. 8A) and IL-5 (FIG. 8B) when re-stimulated ex vivo by OVA.

Figure 9:
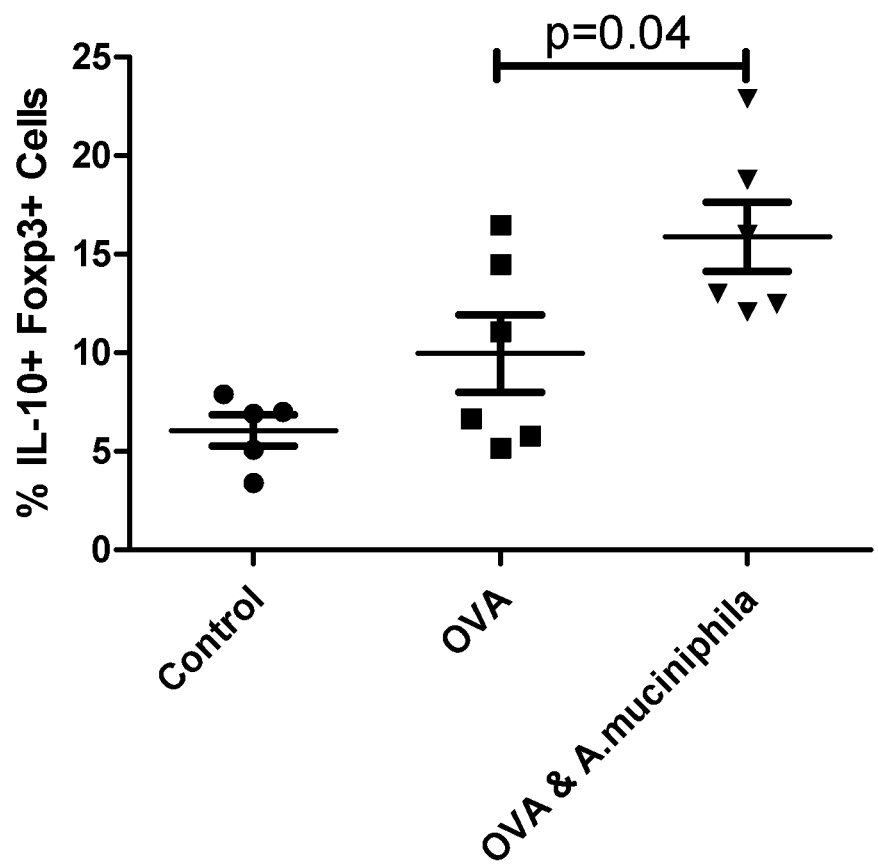

FIG. 9 shows that there are more regulatory lymphocytes within lung tissue of *Akkermansia muciniphila* fed animals.

Figure 10:
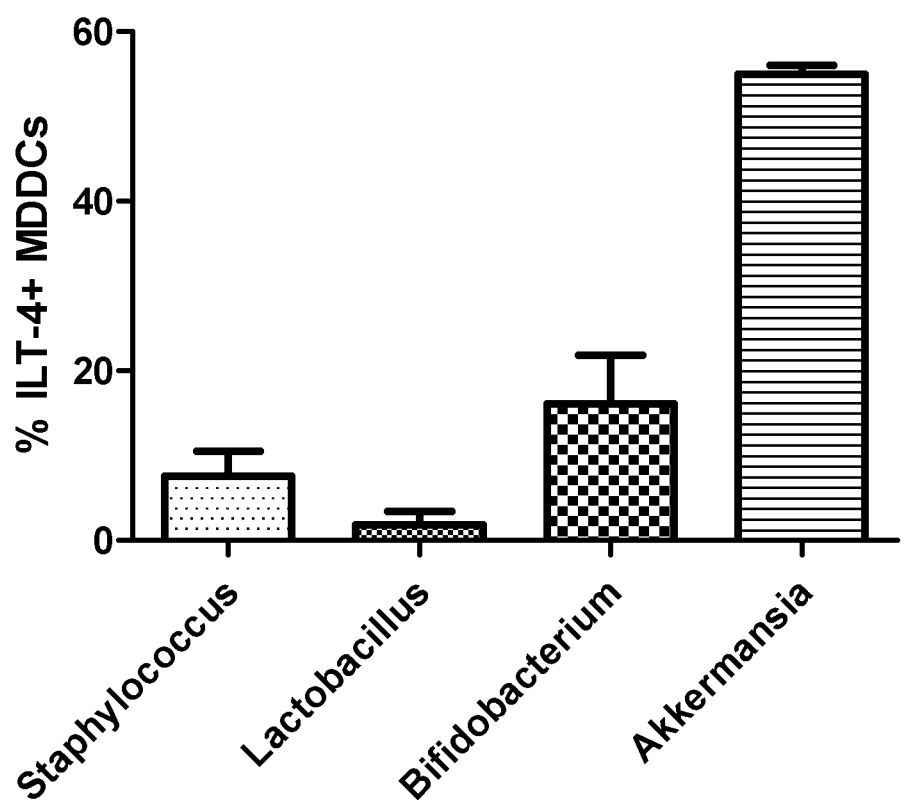

FIG. 10 is a graph illustrating the ability of *Akkermansia muciniphila* to induce LILRB2 (ILT4) expression by human dendritic cells.

Figure 11:
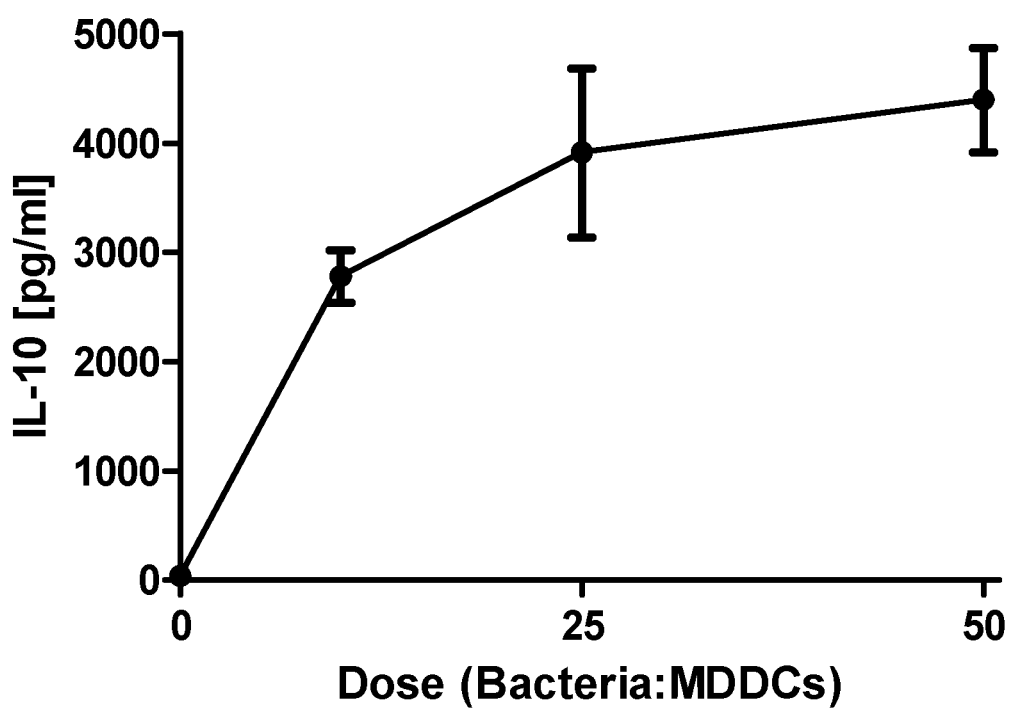

FIG. 11 is a graph illustrating the ability of *Akkermansia muciniphila* to induce IL-10 secretion in a culture of human peripheral blood monocytes after generation of dendritic cells by exposure to GM-CSF and IL-4 for 6 days and contact with *Akkermansia muciniphilia* for 24 hours.

DETAILED DESCRIPTION

As indicated above, the present invention provides a composition comprising one or more *Akkermansia muciniphila* strains for use in the prophylaxis and/or treatment of undesirable inflammatory activity wherein said inflammatory activity is not caused by a metabolic disorder and/or obesity.

Of particular interest is that the invention is applicable to undesirable inflammatory activity remote from the gastrointestinal tract. Such undesirable inflammatory activity of concern may be airway inflammatory activity such as that seen in the case of asthma including exacerbations of asthma, COPD including exacerbations of COPD and eosinophilic COPD, infection-associated inflammation, allergen-induced inflammation, allergic rhinitis or chronic rhinosinusitis. In an especially preferred embodiment, the invention thus provides a composition comprising one or more *Akkermansia muciniphila* strains for use in the prophylaxis and/or treatment of airway inflammation of asthma, especially in asthma patients with a lower than normal level of *Akkermansia muciniphilia* in the gut. As indicated above, of particular interest in relation to such use of *Akkermansia muciniphilia* are severe asthmatics. Asthma patients with a lower than normal gut level of *Akkermansia muciniphila* may be conveniently pre-identified by application of various quantitative diagnostic tests to faecal samples as further discussed below.

By way of example, it is envisaged that the invention may also find application for use in the prophylaxis and/or treatment of any of the following: systemic inflammatory disease such as rheumatoid arthritis; undesirable inflammatory activity associated with an autoimmune disorder; undesirable skin inflammatory activity such as associated with atopic dermatitis or psoriasis and inflammatory activity associated with an infection or cancer or immunotherapy thereof. It may be applied, for example, for use in the prophylaxis and/or treatment of undesirable exacerbations of respiratory inflammatory activity due to bacterial or viral infections.

While use of the invention in relation to undesirable upper or lower respiratory inflammatory activity represents an embodiment of especial interest, its use in relation to undesirable gastrointestinal inflammatory disorders is not excluded, for example use in the prophylaxis and/or treatment of undesirable gastrointestinal inflammatory activity as observed with, for example, inflammatory bowel disease such as Crohn's disease or ulcerative colitis, irritable bowel syndrome, pouchitis, post-infection colitis or inflammation associated with gastrointestinal cancer. It may also find use in relation to diarrhoeal disease due to undesirable inflammatory activity, e.g. the prophylaxis and/or treatment of diarrhoeal disease due to an infectious bacterial agent such as *E.coli, Clostridium difficile* associated diarrhoea, Rotavirus associated diarrhoea or post-infective diarrhoea.

The one or more *Akkermansia muciniphila* strains employed may be naturally-occurring strains derived from human faeces or biopsies, or naturally-occurring variants thereof, which have the desired immunomodulatory effect in the human gut. Genetically modified mutants of naturally-occurring *Akkermansia muciniphila* strains may also be employed provided they retain the desired activity. This may for example be equated with ability to induce ILT4 expression in human dendritic cells in vitro. A suitable assay for this purpose is set out in the exemplification below.

A composition for use in accordance with the invention may additionally include one or more probiotic strains of another bacterial species such as a *Lactobacillus* or *Bifidobacterium*, for example one or more *Akkermansia muciniphila* strains may be combined with *Bifidobacterium longum* infantis 35624 or a variant or mutant thereof as described in EP1141235. However, any other probiotic bacterial strain with immunological benefit might be considered. Alternatively the cells of a different species may be administered sequentially or simultaneously in a different composition.

A composition for use in accordance with the invention may be for direct delivery of one more *Akkermansia muciniphila* strains into the GI tract. Preferably a composition for use in accordance with the invention will be a probiotic composition suitable for direct oral consumption. However, as indicated above a strain-release composition may be provided, which is not ingested but is contacted with a liquid whereby said one or more strains are released into said liquid and the resulting probiotic liquid composition is then consumed. For example, it may be favourable, particularly where the one or more probiotic strains are to be delivered to children, to initially provide the one or more strains in a composition, e g. an oil suspension, within a drinking straw whereby the one or more strains are transferred to a liquid drawn through the straw, e.g. a juice or milk from a drink carton. Such straws housing probiotic strains are described, for example, in European Patent no. 1224128 (Biogaia AB).

A probiotic composition for oral administration in accordance with the invention may include one or more *Akkermansia muciniphila* strains and an ingestible carrier. It may preferably be in the form of a beverage, e.g. drinking yoghurt, juice or milk, or other form of nutritional composition. It may be suitable for human and/or animal consumption. For example the composition may be in the form of a food product such as a yoghurt, cheese, confectionary, cereal or nutritional snack bar. It may be in the form of a nutritional supplement. For example, the one or more probiotic strains may be provided in a nutritional oil suspension, e.g. within a capsule, which will release the probiotic strains in the GI tract.

A composition for use in accordance with the invention may be formulated as a pharmaceutical composition including a pharmaceutically acceptable carrier, preferably such a formulation for oral administration including an ingestible carrier. Such a composition may be in a solid form such as a tablet, pill, powder, granules, troches or suppository. It may be a controlled-release formulation for release of the one or more probiotic strains in the GI tract. It may be in a liquid form, such as a liposomal composition or suspension, e.g. an oil suspension. Such a liquid composition may be provided within an encapsulating substance to provide a capsule or microcapsules, again for release of the one or more probiotic strains in the GI tract. It may be a formulation for aerosol delivery. A pharmaceutical composition for use in accordance with the invention may additionally include a non-microbial therapeutic agent, e.g. a chemical drug entity or a therapeutic biologic, suitable for the prophylaxis and/or treatment of the undesired inflammatory activity of concern or an associated condition.

A composition for use in accordance with the invention will be formulated to provide an appropriate unit dosage of colony-forming units (cfu). This will vary with the form of administration and may be varied, for example, depending on whether the individual to be treated is a child or adult. For example a dosage of at least about $10^4$ cfu, more preferably at least about $10^5$ cfu or at least about $10^6$ cfu, e.g. about $10^6$-$10^{10}$ cfu may be contemplated at least once per day. Administration will desirably be continued so that the level of *Akkermansia muciniphila* in the GI tract is at least restored to or maintained at around the normal level to be expected for a healthy individual.

*Akkermansia muciniphila*, e.g. *Akkermansia muciniphila* Derrien et al. (ATTC® BAA835™) isolated from human faeces and obtainable from the ATCC as a freeze dried preparation, or *Akkermansia muciniphilia* similarly isolated from human faeces or biopsies, may be grown anaerobically in a mucin-based medium as previously described by Derrien et al. (11) and subsequently incorporated into an appropriate composition for administration as discussed above. For example, *Akkermansia muciniphila* thus cultured may be washed and at least initially suspended in anaerobic phosphate buffered saline (PBS), including 25% (v/v) glycerol, e.g. to an end concentration of $10^{10}$ cfu/ml under strict anaerobic conditions. Storage may be at −80° C. with subsequent thawing and possible further dilution, e.g. with anaerobic PBS, as previously described (15, 16).

Due to the oxygen sensitivity of *Akkermansia muciniphila*, storage prior to use in accordance with the invention will be such as to protect from contact with air. Storage may be for example within lipid gels or drops.

Compositions for use in accordance with the invention will generally be stored prior to use in a sealed container or packaging to aid avoidance of prolonged contact with air. Storage may be for example in the form of a digestible solid composition, e.g. pills, provided in sealed compartments of a blister pack.

A composition for use in accordance with the invention by delivery to the GI tract may additionally be supplemented with one or more prebiotic substances. Such substances are recognized to promote growth of one or more probiotic strains in the GI tract, but need not be metabolized by a human. The term 'prebiotic' will be understood to refer to any non-viable food component that can be specifically fermented in the colon by indigenous bacteria and which is considered of positive value. Types of prebiotics of interest include non-digestible oligosaccharides including those containing one or more of fructose, xylose, galactose, glucose and mannose. Soya may be employed as a prebiotic. The combined administration of a bacterial strain with one or more prebiotic substances may enhance the growth of the strain in vivo resulting in a more pronounced health benefit, and is termed synbiotic.

It may be particularly preferred to employ a prebiotic substance which will promote growth in the GI tract of *Akkermansia muciniphila*. By way of example, it has been shown that oligofructose will promote growth of *Akkermansia muciniphila* in the GI tract of mice (16). It can be extrapolated that oligofructose, (e.g. a commercially available oligofructose preparation such as an Orafti® oligofructose preparation, e.g. Orafti® P95 as supplied by Beneo GmbH) may be a useful component to be administered as a prebiotic with one or more *Akkermansia muciniphila* strains in applying the invention. A prebiotic may be administered in the same composition or separately, either simultaneously or sequentially.

In a further aspect of the invention, there is provided a prebiotic substance, e.g. an oligofructose as discussed above, capable of promoting growth of *Akkermansia muciniphila* in the GI tract for use in the prophylaxis and/or treatment of undesirable inflammatory activity wherein said inflammatory activity is not caused by a metabolic disorder and/or obesity. Such inflammatory activity of interest can be expected to be accompanied by below normal level of *Akkermansia muciniphila* in the GI tract and the prebiotic may be administered to raise or substantially maintain the level of *Akkermansia muciniphila*, preferably so that it is restored to or maintained at or about the normal level for a healthy individual. The undesirable inflammatory activity may be any undesirable inflammatory activity as discussed above, especially for example undesirable airway inflammatory activity such as associated with asthma, COPD, eosinophilic COPD, infection-associated inflammation, allergen-induced inflammation, allergic rhinitis or chronic rhinosinusitis.

In an additional aspect of the invention, preferably compositions containing *Akkermansia muciniphilia* are employed as described above in combination with a diagnostic test to determine *Akkermansia muciniphila* abundance in an individual with an aim of treating identified *Akkermansia muciniphilia* deficiency. Such a test may take the form of faecal bacterial microbiome 16S rRNA gene sequencing, PCR specific detection of *Akkermansia muciniphilia* DNA or application of other nucleic acid hybridisation or sequencing technologies, or specific culture on selective media, for specific detection of Akkermansia muciniphilia. Using the 16s sequencing data, the 75% percentile for relative abundance of *Akkermansia muciniphila* in severe asthma patients is 0.01422, which means that 1.422% of identifiable sequences are *Akkermansia muciniphila*. This suggests that *Akkermansia muciniphila* treatment may be most effective in asthma patients whom have a relative abundance of less than about 1.4%. Using the PCR method, the 75% percentile for *Akkermansia muciniphila* in severe asthma patients is 60.1 copy number/ng DNA, suggesting that *Akkermansia muciniphila* treatment may be most effective in asthma patients whom have a detected copy number of less than about 60 per ng of total bacterial DNA.

The invention will be more clearly understood from the following examples.

EXAMPLES

It has been found, for the first time, that *Akkermansia muciniphila* levels are significantly reduced in faecal samples from asthma patients displaying partly controlled or uncontrolled asthma symptoms. Furthermore, consumption of *Akkermansia muciniphila* has been found to significantly reduce recruitment of disease-causing cells to the lungs in four different murine models of respiratory inflammation. In addition, *Akkermansia muciniphila* has immunomodulatory effects; it can modulate cytokine secretion by human dendritic cells in vitro. Indeed, stimulation of the inhibitory molecule LILRB2 (ILT4) by *Akkermansia muciniphila* is surprisingly significantly higher than that observed for other commensal microbes typically used as probiotics.

Four murine models for respiratory inflammation were employed to look at both primarily neutrophil and eosinophil driven responses.

Neutrophils are a type of phagocyte and are normally found in the bloodstream. During the beginning (acute) phase of inflammation, particularly as a result of bacterial infection, environmental exposure, and some cancers, neutrophils are one of the first-responders of inflammatory cells to migrate towards the site of inflammation. They migrate through the blood vessels, then through interstitial tissue, following chemical signals in a process called chemotaxis. They are the predominant cells in pus, accounting for its whitish/yellowish appearance. Neutrophils release a wide range of proteins, which help to destroy a pathogen, but also have detrimental effects on host cells at higher concentrations. Asthma and asthma exacerbations can be associated with high neutrophil or high eosinophil numbers within the lung, both of which contribute to the disease.

Eosinophils are white blood cells and one of the immune system components responsible for combating parasites and certain infections. Along with mast cells, they also control mechanisms associated with allergy and asthma. The presence of eosinophils in the lung or skin is associated with disease. Eosinophils persist in the circulation for 8-12 hours, and can survive in tissue for an additional 8-12 days in the absence of stimulation. Eosinophils are important mediators of allergic responses and asthma pathogenesis and are associated with disease severity. Following activation, eosinophils release a range of powerful molecules including cationic granule proteins, reactive oxygen species, lipid mediators, enzymes, growth factors and cytokines. Many of the mediators released by eosinophils are toxic at high levels to host cells.

Evidence from murine house dust mite (HDM) re-challenge model experiments presented here and from recent literature demonstrate that it is possible to identify two distinct populations of eosinophils in lung tissue based on Siglec-F expression. A lung resident population of eosinophils has been identified as Siglec-$F^{int}$, while an inflammatory population, infiltrating after HDM re-challenge, is identified as $SiglecF^{high}$. Inflammatory eosinophils are IL-5-dependent and have been shown to facilitate skewing towards a Th2 response, while the resident population are IL-5-independent and are thought to have a more regulatory function responsible for inhibiting pro-allergic functions of dendritic cells (19, 20). Mesnil and colleagues demonstrated that it is also possible to stratify patients with asthma from healthy individuals based on the presence of resident and inflammatory eosinophil populations within the lung with asthmatics having a higher number of the inflammatory eosinophil population; hence there has been suggested a relationship between eosinophil phenotype and disease.

Assays described below measured IgE, ILT4, IL-4, IL5, IL-10 and Foxp3$^+$ regulatory T cells.

IL-4 is a 15-kd monomer (129 amino acids) produced by Th2 cells, basophils, mast cells, and eosinophils. There are two types of IL-4 receptors. Type I IL-4R binds only IL-4 and consists of 2 receptor chains: IL-4Rα (CD124) and the common γc (CD132). Type II IL-4R binds IL-4 and IL-13 and consists of the IL-4Rα and the IL-13Rα1 chains. A pleiotropic cytokine, IL-4 promotes allergic conditions and the protective immune response against helminths and other extracellular parasites. IL-4 is the major stimulus of Th2-cell development; it also suppresses Th1-cell development and induces IgE class-switching in B cells. IL-4 increases the expression of class II MHC molecules on B cells, upregulates B-cell receptors, increases expression of CD23, prolongs lifespans of T and B cells in culture, and mediates tissue adhesion and inflammation. IL-4 and IL-4Rα knockout mice have defects in Th2-cell differentiation and reduced serum levels of IgG1 and IgE.

IL-5 is mainly produced by CD4+ Th2 cells, activated eosinophils, mast cells, CD8+ Tc2 cells, γδ T cells, NK cells, NKT cells, and CD4-ckit-CD3ε-IL-2Rα+ cells in Peyer patches. Its receptor shares the β-chain (CD131) with IL-3 and GM-CSF. IL-5 promotes proliferation, activation, differentiation, survival, and adhesion of eosinophils. Th2 cells that secrete IL-5 recruit eosinophils and contribute to the induction of airway hyper-reactivity in patients with asthma. Levels of IL-5, Th2 cells, and eosinophils are increased in bronchoalveolar lavage and correlate with asthma severity. IL-5-deficient mice develop normally but are resistant to induction of experimental asthma, display reduced expulsion of *Nippostrongylus brasiliensis*, and have fewer IgA+ antibody cells in the lamina propria compared with control mice. Clinical trials targeting IL-5 have produced mixed results, but patients with refractory eosinophilic asthma were reported to have reduced numbers of exacerbations and eosinophils in sputum and blood and increased quality of life (21).

FOXP3 (forkhead box P3) also known as scurfin is a protein involved in immune system responses. A member of the FOX protein family, FOXP3 is a master regulator (transcription factor) in the development and function of regulatory T cells. Regulatory T cells prevent excessive immune responses, which could damage host tissues. In autoimmune disease, a deficiency of regulatory T cell activity can allow other autoimmune cells to attack the body's own tissues. Defects in regulatory T cell induction and/or activity have been demonstrated in multiple allergy and asthma models.

Immunoglobulin-like transcript 4 (ILT4) can be expressed on dendritic cells and is bound by HLA-G. The engagement of ILT4 by HLA-G tetramers prevents the up-regulation of costimulatory molecule expression, inhibits dendritic cell maturation and promotes the differentiation of anergic/suppressor CD4$^+$ T cells. In addition, differentiation of the critical immunoregulatory IL-10 secreting T cell subset, Tr1 cells, is dependent on the IL-10-dependent ILT4/HLA-G pathway (22). These Tr1 cells play a central role in tolerance induction and contribute to the suppression of aberrant inflammatory activity, such as that observed in the inflamed lung of asthma patients.

IL-10 is an anti-inflammatory cytokine that is an important regulator of several aspects of immune responses (23). The IL-10 gene maps to a cytokine cluster that includes the genes IL-19, IL-20, IL-24, and IL-26 on chromosome 1q31-32. IL-10 is produced mainly by monocytes, T cells (mainly Tr1 cells), B cells, NK cells, macrophages, and dendritic cells. IL-10 is secreted as a homodimer that consists of 2 subunits, each of 178 amino acids with a molecular weight of approximately 18 kd. IL-10 directly affects antigen-presenting cell functions by down-regulating the expression of MHC class II and costimulatory molecules on the surface of macrophages and monocytes. IL-10 inhibits the expression of many proinflammatory cytokines, chemokines, and chemokine receptors and mediates allergen tolerance in allergen-specific immunotherapy and after exposure to high doses of allergen. In addition to these indirect effects, IL-10 directly affects T-cell activation by suppressing CD28, CD2, and signaling of the inducible T-cell costimulator via the tyrosine phosphatase SHP-1. In contrast with its inhibitory effects on T cells, IL-10 promotes survival, proliferation, and differentiation of human B cells and increases the production of IgG4. Several mouse models demonstrate the importance of IL-10 in regulation of the inflammatory response. IL-10 knockout mice develop normal lymphocyte and antibody responses but have reduced growth, are anemic, and spontaneously develop chronic colitis.

Presence of elevated Immunoglobulin E (IgE) levels in serum is regarded as an integral part of the inflammatory cascade observed in allergic diseases such as asthma. Induction of allergen-specific IgE can be detected in animal models of allergic pulmonary inflammation as well as in human asthmatics and is an indication of the initiation of the relevant cellular (T and B cell axis) and humoral mechanisms that drive development of allergy. Hence, modulation of the allergen-specific IgE response by therapeutic intervention points to modulation of the mechanisms that fundamentally underpin development of allergy. In addition, the importance of elevated levels of IgE is demonstrated by the fact that anti-IgE antibody therapies have been shown to be important in reducing severe asthmatic exacerbations (24).

Example 1

Abundance of Bacterial Species in Faeces From Asthma Patients

Freshly voided faecal samples were obtained from asthma patients and were stored at −80 C until analysis. Upon thawing, DNA was extracted from the faecal samples and the 16s rRNA V4 region was amplified by PCR. These PCR products were sequenced using MiSeq and identical sequences were grouped together into operational taxonomic units (OTUs). OTUs were aligned to known 16s sequences and the relative abundance for each OTU was calculated.

In addition to microbiome analysis, clinical data was collected from all asthma patients. In particular, the level of symptom control was assessed using an internationally validated questionnaire, which asked the following questions.

Do you experience any of the following?
1. Asthma daytime symptoms more than 2 times per week?
2. Waking at night due to asthma symptoms?
3. Use of rescue medications more than 2 times in the previous week?
4. Exercise or physical activity limited due to asthma symptoms?

A "No" answer to all four questions means that the asthma patient should be considered as well controlled. A "Yes" answer to one or two questions means that the patient is partly controlled, while a "Yes" answer to three or four questions means that the patient has uncontrolled asthma symptoms.

Figure 1A:
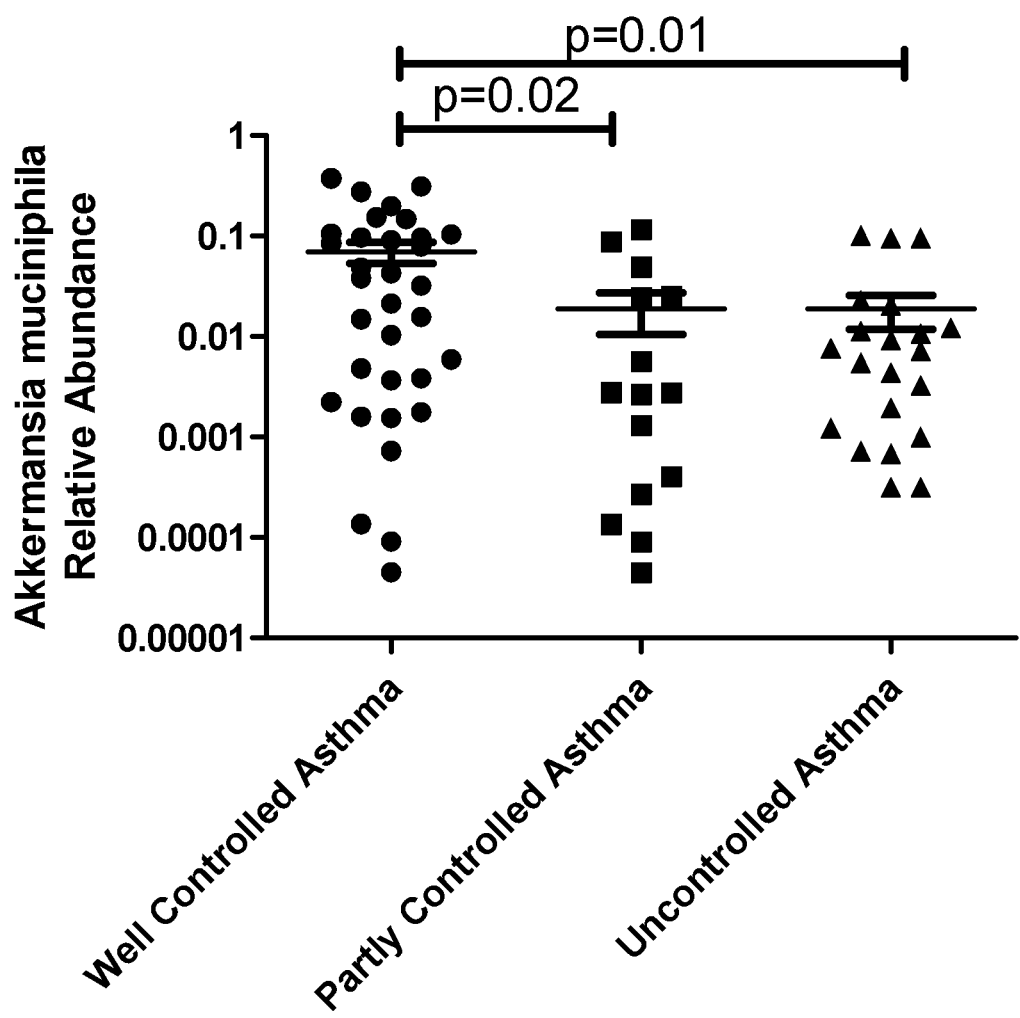
FIG. 1A illustrates that *Akkermansia muciniphila* levels decrease in uncontrolled asthma patients with increased symptom severity, while FIG. 1B demonstrates that the decrease in *Akkermansia muciniphila* levels is unrelated to obesity. The data is represented as relative abundance of *Akkermansia muciniphilia*, based on 16s rRNA gene sequencing employing faecal samples.
Figure 1B:
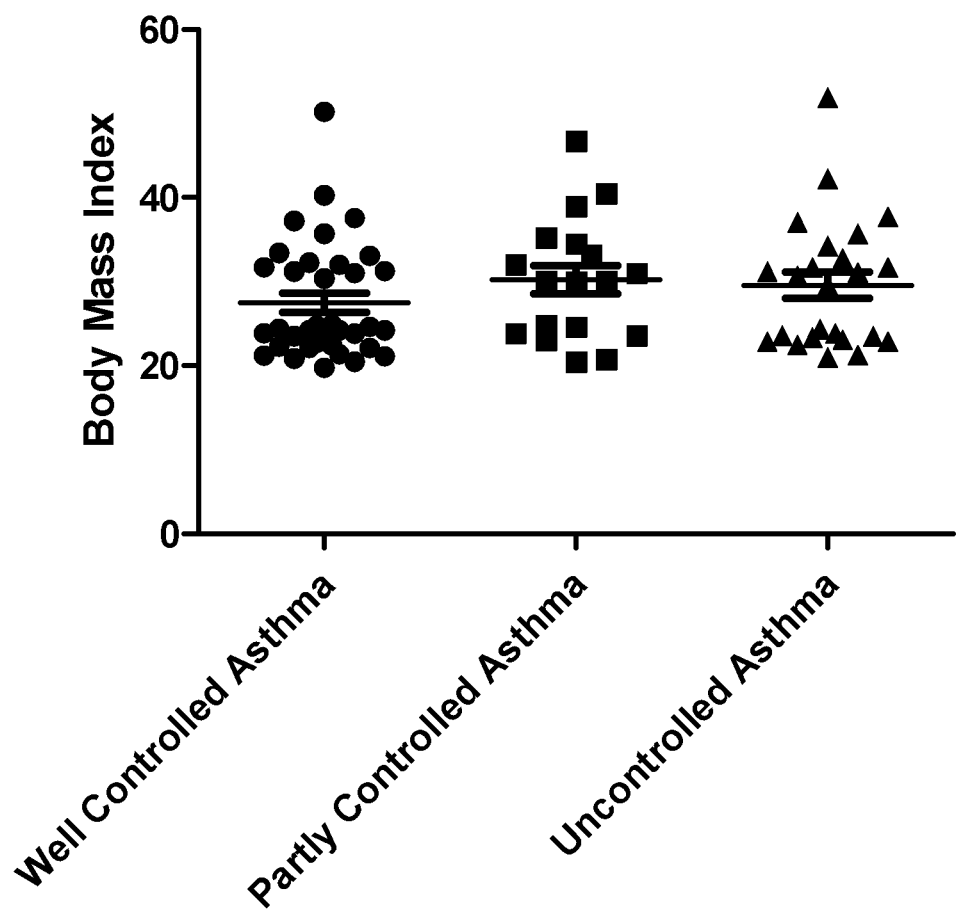

Surprisingly, when the microbiome data from asthma patients was divided into controlled, partly controlled and uncontrolled categories, it was discovered that *Akkermansia muciniphila* levels were significantly lower in patients with partly or uncontrolled asthma symptoms (FIG. 1A). Importantly, *Akkermansia muciniphila* levels in controlled asthma patients were similar to that observed for healthy volunteers, representing approximately 8% of all the sequences obtained from these individuals. Thus, *Akkermansia muciniphila* is numerically one of the most dominant species within the colon. A reduction to approximately 1-2% of the microbiome in patients with uncontrolled asthma symptoms is an enormous decrease with potentially critical health consequences. As noted above, this is the first time that a relationship between decreased gastrointestinal levels of *Akkermansia muciniphila* has been linked to the severity of a respiratory disease, regardless of the presence of obesity or atopy.

Figure 2:
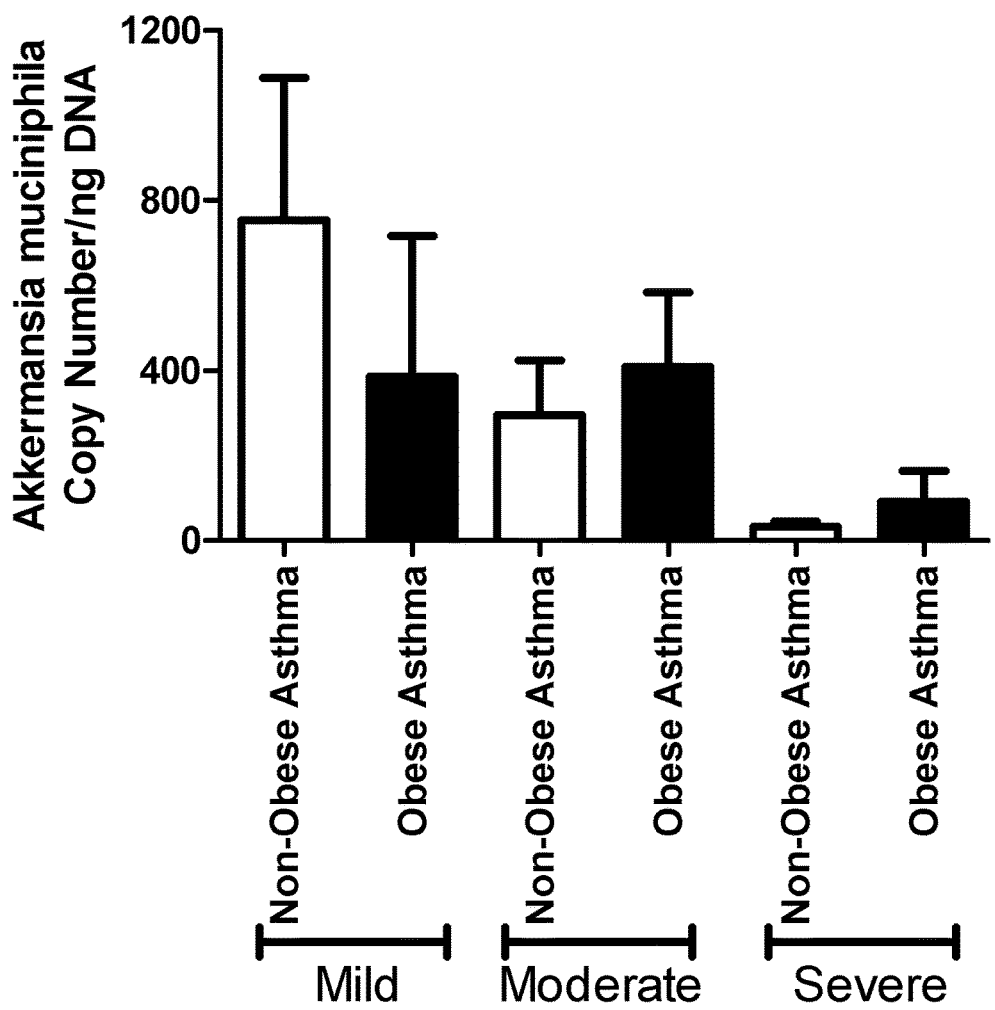
FIG. 2 shows that *Akkermansia muciniphila* levels decrease in asthma patients with severe disease which is unrelated to obesity relying on quantitative PCR and *Akkermansia muciniphilia*-specific primers to analyse *A. muciniphila* genomic DNA in faecal samples from asthma patients with varying severity of asthma. A patient was included to the severe asthma group if he/she fulfilled one or both major and at least two minor criteria as defined by Chung et al (18). Patients who did not fulfil these criteria were enrolled to mild or moderate asthma groups. The data is represented as genome copy number per ng of DNA, assessed using quantitative PCR.

In order to confirm the 16s sequencing data, *Akkermansia muciniphila* levels in faecal samples were also quantified using PCR. Quantitative PCR analysis was performed using an Applied Biosystems 7900 HT Fast Real-Time PCR system and the *Akkermansia muciniphila*-specific primer sequences used were AM1 5'CAG CAC GTG AAG GTG3' (SEQ. ID. No. 1) and AM2 5'CCT TGC GGT TGG CTT CAG3' (SEQ. ID. No. 2). The experimental cycling conditions were: 40 cycles of 50° C. for 2 min, 95° C. for 10 min, 95° C. for 15 sec, 60° C. for 1 min. The quantitative PCR results were identical to the 16s sequencing data (FIG. 2).

Example 2

*Akkermansia muciniphila* is Protective in the Murine Models of Asthma

In order to understand if *Akkermansia muciniphila* has the potential to directly influence lung inflammatory responses, we performed a murine house dust mite respiratory inflammation study. House dust mite (HDM) allergens are one of the most common aeroallergens that asthma patients are allergic to. Intranasal (i.n.) administration of HDM extract to mice results in lung inflammatory responses. We administered HDM extract i.n. on day 0 (1 μg), followed by higher dose i.n. administrations on days 7, 8, 9, 10 and 11 (10 μg each day). This model is considered to be an acute challenge model. Animals were euthanized on day 14 and bronchoalveolar lavages (BAL) were obtained for enumeration of inflammatory cells. *Akkermansia muciniphila* (from a stock culture of the inventors) was administered daily (approximately $1 \times 10^8$ cells) by oral gavage, beginning at day −5 until the end of the study. *Akkermansia muciniphila* was grown for 16 hours in 10 mL aliquots of anaerobic Mucin v3 media (10% inoculation) at 37° C. Nitrogen (and boiling) was used to remove the presence of oxygen from Mucin v3 media. Mucin v3 media contains peptone, yeast extract, $KH_2PO_4$, NaCl, $(NH_4)SO_4$, $MgSO_4$, $CaCl_2$, $NaHCO_3$, glucose, mucin type II, hemin, cysteine and water. Negative control animals received NaCl i.n. on the same days as the positive control animals received HDM extracts i.n.

Figure 3A:
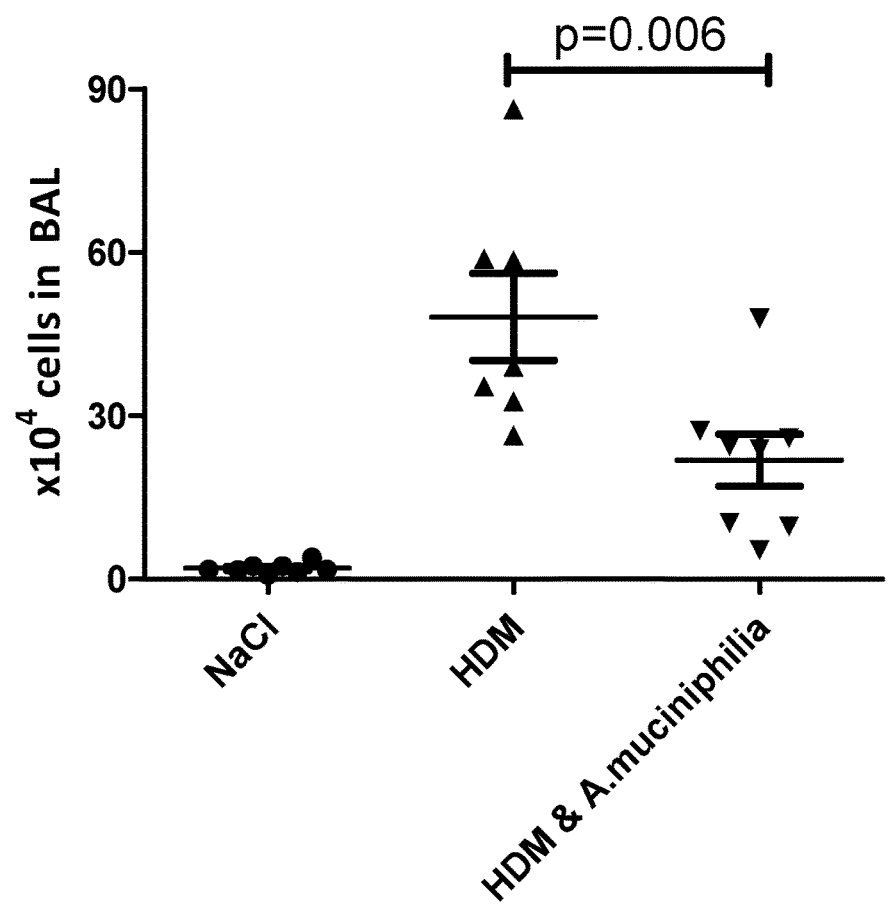
FIG. 3A is a graph showing the suppressive effect of *Akkermansia muciniphila* feeding on inflammatory cell recruitment to the lungs of house dust mite (HDM) extract acutely challenged mice, with FIG. 3B highlighting the decrease in inflammatory neutrophils.
Figure 3B:
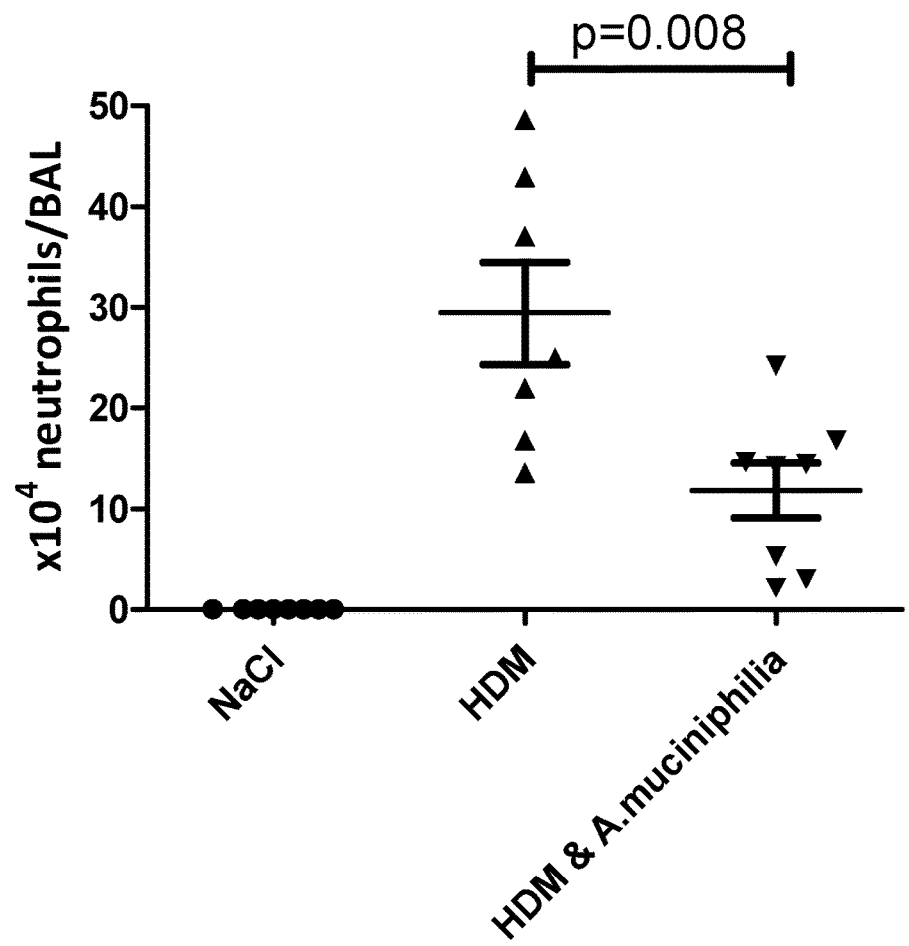

Surprisingly, oral administration of *Akkermansia muciniphila* significantly protected against inflammatory cell recruitment into the BAL of animals exposed to HDM extract, compared to animals that received HDM extract alone (FIG. 3A). When microscopic differential cell counts were performed, it was clear that the reduced BAL inflammatory cell count in *Akkermansia muciniphila* treated animals was primarily due to a reduced migration of neutrophils, which is the dominant infiltrating proinflammatory cell type in this model (FIG. 3B).

Chronic and Re-challenge Models

Chronic intranasal challenges with proteolytically active allergens such as house dust mite (HDM) extract have been shown to elicit allergic inflammatory changes within the lung (25). HDM extract is composed of many different substances that include proteolytic enzymes (Derp) and LPS and can therefore cause inflammatory responses that involve a vast array of interactions between structural and immune cells (lymphocytic and myeloid) and mediators (26-28). In the experiments now presented, female BALB/c mice (8-10 weeks of age) were intra-nasally challenged with either sterile saline or 25 µg of HDM extract in a volume of 50 µl (Greer labs, US, batch number: 218862) 5 days a week, for 3 weeks (sensitization period, days 1-19). This model is different to that described above and is considered to be a chronic model of respiratory inflammation.

The resulting pulmonary inflammation in the HDM sensitized mice was allowed to partially resolve for a period of 2 weeks (days 20 to 33). At the end of the resolution period (day 34), mice were intra-nasally challenged with either saline or re-challenged with HDM (100 µg) in a total volume of 50 µl. HDM re-challenge in this model has been shown to result in granulocytic and lymphocytic infiltration into the lung over a 7 day period (days 34 to 40). The pulmonary eosinophilic response in HDM re-challenged mice is significantly different to that of saline challenged animals from 24 hrs (day 35) and peaks at 168 hrs (day 40) post HDM re-challenge. In the experiments presented here, mice were dosed by oral gavage (0.2 ml) with either media control or *Akkermansia muciniphila* once a day, starting on day 20 (post cessation of HDM sensitization). Oral dosing continued throughout the resolution period and post HDM re-challenge and finally ceasing on day 39. Groups of mice were sacrificed at pre-determined time-points during the resolution phase of the experiment (day 28) and post HDM re-challenge (4 hrs (day 34), 24 hrs (day 35) and 168 hrs (day 40). Cells present in the broncho-alveolar lavage fluid (BALF) and lung tissue were analyzed and quantified using multi-colour flow cytometry.

Figure 4A:
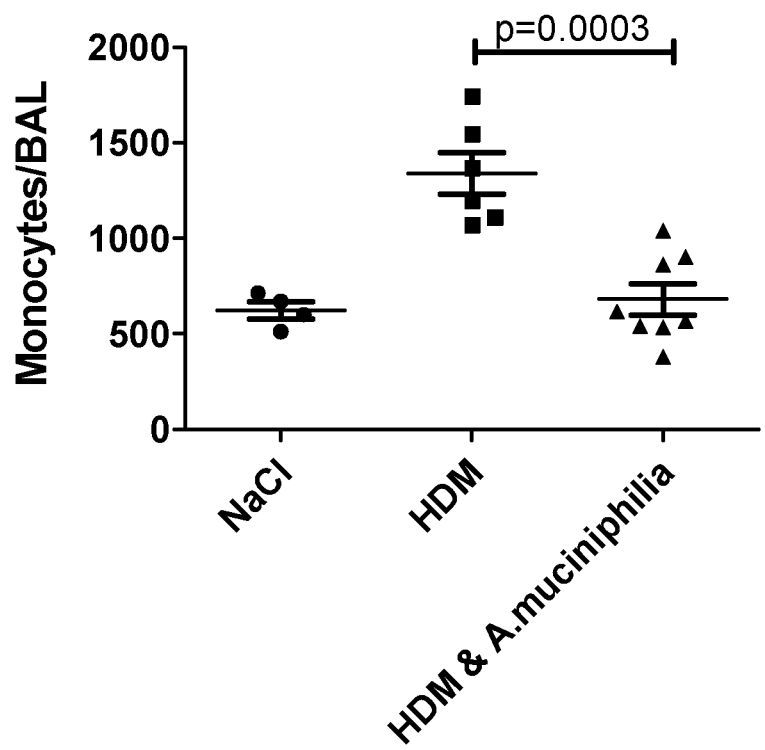
FIG. 4A shows the suppressive effect of *Akkermansia muciniphila* feeding on inflammatory innate cell recruitment to the lungs during the healing/resolution phase following chronic challenge of mice with house dust mite extract, with FIG. 4B highlighting the decrease in lymphocyte subsets.
Figure 4A:
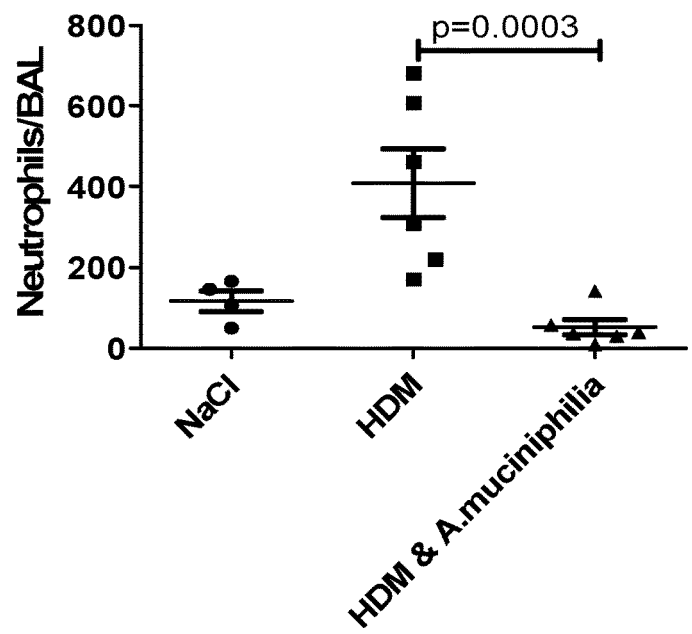
Figure 4A:
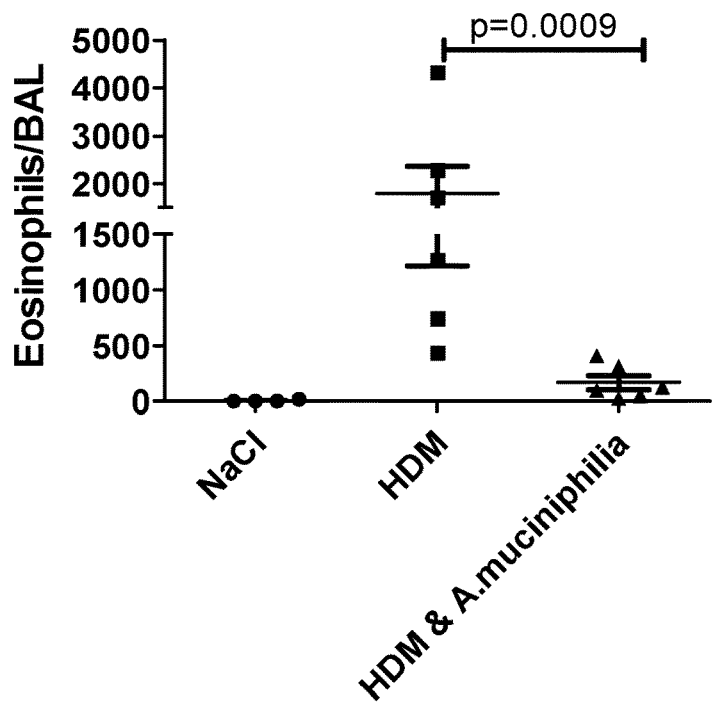
Figure 4B:
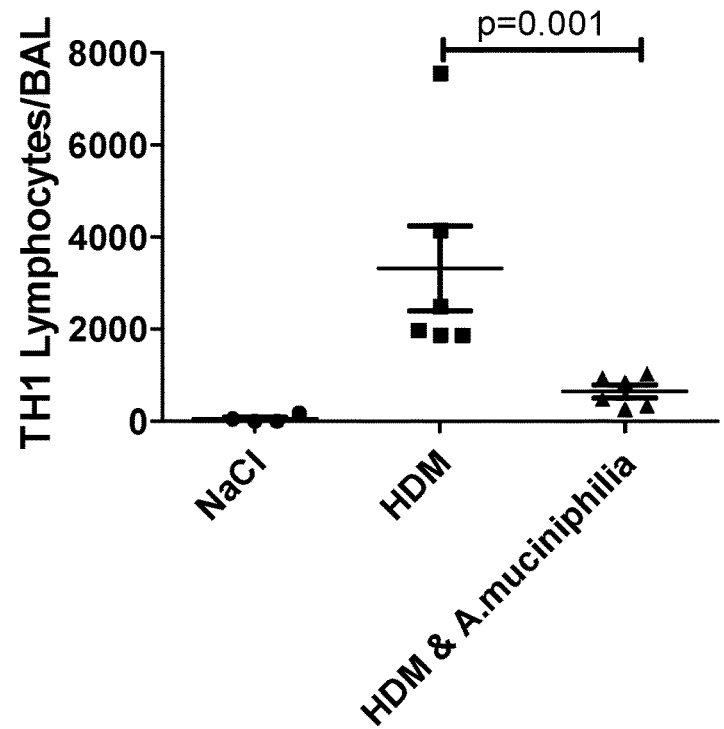
Figure 4B:
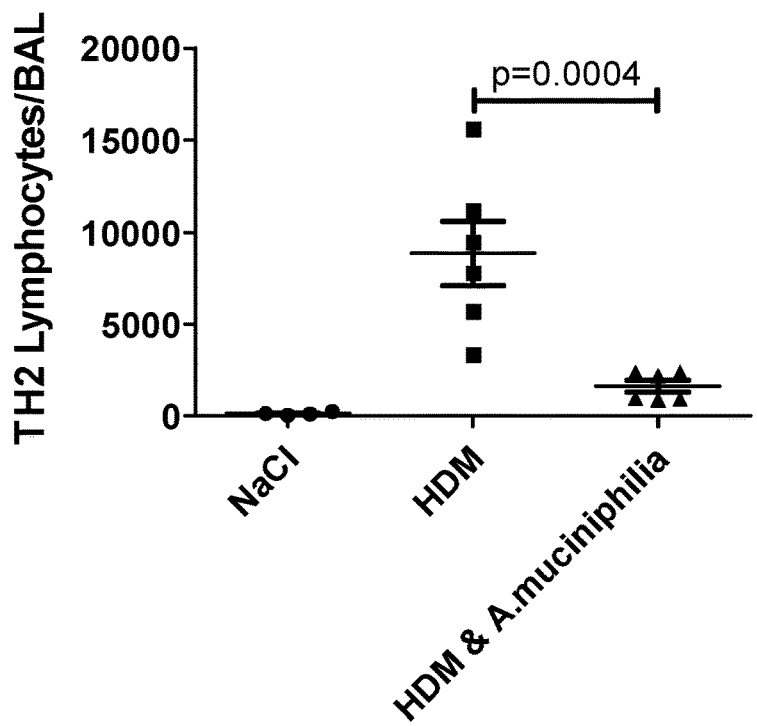
Figure 4B:
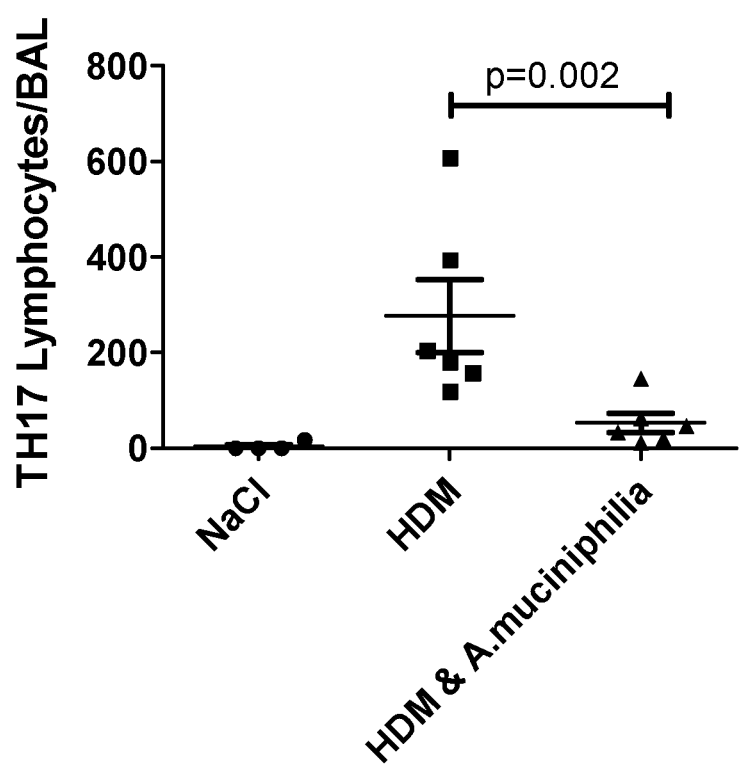

*Akkermansia muciniphila* feeding resulted in enhanced clearance of inflammatory cells (granulocytic and lymphocytic) present in the BALF during the resolution phase of the experiment (FIGS. 4A and 4B). Infiltration of eosinophils into the BALF after HDM re-challenge was also significantly suppressed by *Akkermansia muciniphila* feeding (FIG. 5A). Numbers of infiltrating inflammatory eosinophils (Siglec-F$^{high}$ eos) were also significantly inhibited in the lung tissue of mice fed with *Akkermansia* (FIGS. 5B and C). *Akkermansia muciniphila* was also able to significantly inhibit the induction of HDM-specific IgE in the serum at day 40 (168 hrs post HDM re-challenge (FIG. 6)).

The HDM mouse model examines the response to an allergenic extract, the inventors also wished to test the influence of *Akkermansia muciniphila* in an eosinophil dominant model of lung disease, which is driven by a single allergen. Mice were sensitized to the protein ovalbumin (OVA) by intraperitoneal injection (with the adjuvant alum) on days 0, 14 and 21 followed by repeated OVA aerosol challenge on days 26-28. Animals were euthanized on day 29 for analysis of lung disease parameters. *Akkermansia muciniphila* purchased from the ATCC [*Akkermansia muciniphila* Derrien et al. (ATTC® BAA-835™)] was administered by oral gavage (approximately 1×10$^8$ cells) for the duration of the study. *Akkermansia muciniphila* was again grown for 16 hours in 10 mL aliquots of anaerobic Mucin v3 media (10% inoculation) at 37° C.

Surprisingly, *Akkermansia muciniphila* significantly protected against inflammatory cell recruitment into the BAL of animals exposed to OVA, compared to animals that received OVA alone (FIG. 7A). When microscopic differential cell counts were performed, it was clear that the reduced BAL inflammatory cell count in *Akkermansia muciniphila* treated animals was primarily due to a reduced migration of eosinophils, which is the dominant infiltrating proinflammatory cell type in this murine model (FIG. 7B).

Isolated cells from excised lung tissue were also re-stimulated with OVA in vitro to assess the cytokine response to OVA. Lymphocytes from OVA allergic animals secreted significantly more IL-4 and IL-5 in response to OVA compared to lymphocytes from non-allergic animals (FIGS. 8A and 8B), as expected. However, this increase in IL-4 and IL-5 secretion was not observed with lung tissue cells from animals treated with *Akkermansia muciniphila* by oral gavage.

Detailed analysis of the lung tissue lymphocytes revealed that there are significantly more Foxp3+ regulatory T cells that secrete IL-10 in the lung tissue of mice administered *Akkermansia muciniphila* (FIG. 9). These cells typically are potent suppressors of aberrant inflammatory responses. Thus increase in these cells within the lung may account for the protective efficacy of *Akkermansia muciniphila*.

Example 3

*Akkermansia muciniphila* Induces Immune Regulatory and Anti-inflammatory Responses in Dendritic Cells A further study was carried out with a view to elucidating how the dramatic and unexpected anti-inflammatory lung effect could be induced by a bacterium present within the gastrointestinal tract. Dendritic cells are one of the important cell types within the gut mucosa, which sample luminal bacteria and induce potent polarizing effects on downstream lymphocyte responses (29). Thus we hypothesized that *Akkermansia muciniphila* stimulated dendritic cells to express high levels of immune regulatory molecules, which would promote the downstream anti-inflammatory effects observed in the lung.

Human monocyte-derived dendritic cells (MDDCs) were generated by culturing human peripheral blood monocytes in GM-CSF and IL-4 for six days. MDDCs were exposed to *Akkermansia muciniphila* for 24 hours and ILT4 cell surface expression was measured by flow cytometry, while IL-10 cytokine secretion was measured by ELISA. *Akkermansia muciniphila* was prepared by growing for 16 hours in 10 mL aliquots of anaerobic Mucin v3 media (10% inoculation) at 37° C. Bacterial cell number was determined by microscopy and bacterial cells were added to MDDCs at a bacterial cell:MDDC cell ratio of 50:1.

*Akkermansia muciniphila* induced ILT4 expression on a very large number of MDDCs (FIG. 10). Surprisingly, *Akkermansia muciniphila* induced ILT4 expression was significantly higher than the effect observed with other probiotic microbes (such as Bifidobacteria or Lactobacilli) or for pathogens such as Staphylococcus aureus (FIG. 10). ILT4 is largely responsible for inducing regulatory T cells, which can secrete IL-10. Increased numbers of IL-10 positive regulatory T cells described in the murine model above may be due to induction of ILT4 expression by dendritic cells. In addition to inducing very high expression of the regulatory cell surface molecule ILT4, *Akkermansia muciniphila* also induced very high levels of IL-10 secretion, another anti-inflammatory molecule (FIG. 11). *Akkermansia muciniphila* was prepared by growing for 16 hours in 10 mL aliquots of anaerobic Mucin v3 media (10% inoculation) at 37° C. Bacterial cell number was determined by microscopy and bacterial cells were added to MDDCs at a bacterial cell:MDDC cell ratio of 10:1, 25:1 or 50:1.

This data suggests that the *Akkermansia muciniphila* protective effect in the lung could be mediated in part via its induction of regulatory dendritic cells within the gut, which promote the local polarization of regulatory lymphocytes and these regulatory lymphocytes can then migrate to other mucosal sites, such as the lung, to dampen proinflammatory responses.

REFERENCES

1. Frei R, Akdis M, O'Mahony L. Prebiotics, probiotics, synbiotics, and the immune system: experimental data and clinical evidence. Curr Opin Gastroenterol. 2015 March; 31(2):153-8.
2. Frei R, Lauener R P, Crameri R, O'Mahony L. Microbiota and dietary interactions: an update to the hygiene hypothesis? Allergy. 2012 April; 67(4):451-61.
3. Dickson R P, Martinez F J, Huffnagle G B. The role of the microbiome in exacerbations of chronic lung diseases. Lancet. 2014 Aug. 23; 384 (9944):691-702.
4. Konieczna P, Akdis C A, Quigley E M, Shanahan F, O'Mahony L. Portrait of an immunoregulatory *Bifidobacterium*. Gut Microbes. 2012 May-June; 3(3):261-6.
5. Tan J, McKenzie C, Potamitis M, Thorburn A N, Mackay C R, Macia L. The role of short-chain fatty acids in health and disease. Adv Immunol. 2014; 121:91-119.
6. Smolinska S, Jutel M, Crameri R, O'Mahony L. Histamine and gut mucosal immune regulation. Allergy. 2014 March; 69(3):273-81.
7. Groeger D, O'Mahony L, Murphy E F, Bourke J F, Dinan T G, Kiely B, Shanahan F, Quigley E M. *Bifidobacterium infantis* 35624 modulates host inflammatory processes beyond the gut. Gut Microbes. 2013 July-August; 4(4):325-39.
8. Lyons A, O'Mahony D, O'Brien F, MacSharry J, Sheil B, Ceddia M, Russell W M, Forsythe P, Bienenstock J, Kiely B, Shanahan F, O'Mahony L. Bacterial strain-specific induction of Foxp3+ T regulatory cells is protective in murine allergy models. Clin Exp Allergy. 2010 May; 40(5):811-9.
9. Karimi K, Inman M D, Bienenstock J, Forsythe P. *Lactobacillus reuteri*-induced regulatory T cells protect against an allergic airway response in mice. Am J Respir Crit Care Med. 2009 Feb. 1; 179(3):186-93.
10. Abrahamsson T R, Jakobsson H E, Andersson A F, Björkstén B, Engstrand L, Jenmalm M C. Low gut microbiota diversity in early infancy precedes asthma at school age. Clin Exp Allergy. 2014 June; 44(6):842-50.
11. Derrien M, Vaughan E E, Plugge C M, de Vos W M. *Akkermansia muciniphila* gen. nov., sp. nov., a human intestinal mucin-degrading bacterium. Int J Syst Evol Microbiol. 2004 September; 54 (Pt 5):1469-76.
12. Derrien M, Van Baarlen P, Hooiveld G, Norin E, Müller M, de Vos W M. Modulation of Mucosal Immune Response, Tolerance, and Proliferation in Mice Colonized by the Mucin-Degrader *Akkermansia muciniphila*. Front Microbiol. 2011 Aug. 1; 2:166.
13. Png, C. W., Linden, S. K., Gilshenan, K. S., Zoetendal, E. G., McSweeney, C. S., Sly, L. I., McGuckin, M. A., and Florin, T. H. J. Mucolytic bacteria with increased prevalence in IBD mucosa augment in vitro utilization of mucin by other bacteria. Am. J. Gastroenterol. 2010; 105: 2420-2428.
14. Dao M C, Everard A, Aron-Wisnewsky J, Sokolovska N, Prifti E, Verger E O, Kayser B D, Levenez F, Chilloux J, Hoyles L; MICRO-Obes Consortium, Dumas M E, Rizkalla S W, Doré J, Cani P D, Clément K. *Akkermansia muciniphila* and improved metabolic health during a dietary intervention in obesity: relationship with gut microbiome richness and ecology. Gut. 2015 Jun. 22.
15. Cani P, Everard A, Belzer C, de Vos W. Use of *Akkermansia* for treating metabolic disorders. WO 2014/075745 filed19 Nov. 2012 and WO 2014/ 076246 claiming priority therefrom filed 15 Nov. 2013.
16. Everard A, Belzer C, Geurts L, Ouwerkerk J P, Druart C, Bindels L B, Guiot Y, Derrien M, Muccioli G G, Delzenne N M, de Vos W M, Cani P D. Cross-talk between *Akkermansia muciniphila* and intestinal epithelium controls diet-induced obesity. PNAS 2013 May; 110: 9066-9071
17. Drell T, Larionova A, Voor T, Simm J, Julge K, Heilman K, Tillmann V, Štšepetova J, Sepp E. Differences in Gut Microbiota Between Atopic and Healthy Children. Curr Microbiol. 2015 August; 71(2):177-83.
18. Chung K F, Wenzel S. European Respiratory Society/American Thoracic Society Severe Asthma International Guidelines Task Force. International ERS/ATS guidelines on definition, evaluation and treatment of severe asthma. Eur Respir J. 2014 43(2):343-73.
19. Mesnil C, Raulier S, Paulissen G, Xiao X, Birrell M A, Pirottin D, Janss T, Starkl P, Ramery E, Henket M, Schleich F N, Radermecker M, Thielemans K, Gillet L, Thiry M, Belvisi M G, Louis R, Desmet C, Marichal T, Bureau F. Lung-resident eosinophils represent a distinct regulatory eosinophil subset. J Clin Invest. 2016; 126:3279-95.
20. Rothenberg M E. A hidden residential cell in the lung. J Clin Invest. 2016; 126:3185-7.
21. Haldar P, Brightling C E, Hargadon, Gupta S, Monteiro W, Sousa A, et al. Mepolizumab and exacerbations of refractory eosinophilic asthma. N Engl J Med. 360 (2009), pp. 973-984).
22. Gregori S, Tomasoni D, Pacciani V, Scirpoli M, Battaglia M, Magnani C F, Hauben E, Roncarolo M G. Differentiation of type 1 T regulatory cells (Tr1) by tolerogenic DC-10 requires the IL-10-dependent ILT4/HLA-G pathway. Blood. 2010 Aug. 12; 116(6):935-44.
23. Akdis M, Burgler S, Crameri R, Eiwegger T, Fujita H, Gomez E, Klunker S, Meyer N, O'Mahony L, Palomares O, Rhyner C, Ouaked N, Schaffartzik A, Van De Veen W, Zeller S, Zimmermann M, Akdis C A. Interleukins, from 1 to 37, and interferon-γ: receptors, functions, and roles in diseases. J. Allergy Clin Immunol. 2011 March; 127(3):701-21.
24. Lin C H, Cheng S L. A review of omalizumab for the management of severe asthma. Drug Des Devel Ther. 2016; 10:2369-78.
25. Johnson J R, Wiley R E, Fattouh R, Swirski F K, Gajewska B U, Coyle A J, Gutierrez-Ramos J C, Ellis R, Inman M D, Jordana M. Continuous exposure to house dust mite elicits chronic airway inflammation and structural remodeling. Am J Respir Crit Care Med. 2004; 169:378-385.

26. Cates E C, Fattouh R, Johnson J R, Llop-Guevara A, Jordana M. Modeling Responses to Respiratory House Dust Mite Exposure. Contributions to Microbiology 2007 (Sjöbring U & Taylor J D editors); 42-67.
27. Gregory L G, Lloyd C M. Orchestrating house dust mite-associated allergy in the lung. Trends Immunol. 2011; 32:402-411.
28. Jacquet A. Innate immune responses in house dust mite allergy. ISRN Allergy 2013:735031
29. Schiavi E, Smolinska S, O'Mahony L. Intestinal dendritic cells. Curr. Opin. Gastroenterol. 2015 March; 31(2): 98-103.

rally-occurring *Akkermansia muciniphila* strain derived from human feces or biopsies, or naturally-occurring variants thereof, which have an immunomodulatory effect in the human gut.

7. The method of claim 1, wherein said one or more *Akkermansia muciniphila* strains are administered simultaneously or sequentially with one or more probiotic strains of another bacterial species.

8. The method of claim 1, wherein said one or more *Akkermansia muciniphila* strains are in a probiotic composition suitable for oral administration.

The invention claimed is:

1. A method for the treatment of airway inflammatory activity in a subject having an airway disorder, the method comprising: administration of one or more *Akkermansia muciniphilia* strains to the gastrointestinal tract of a subject having an airway disorder, wherein the airway inflammatory activity of an airway disorder is selected from the group consisting of asthma, infection-associated inflammation, allergen-induced inflammation, allergic rhinitis and chronic rhinosinusitis, thereby treating the airway inflammatory activity in the subject.

2. The method of claim 1, wherein said airway disorder is asthma.

3. The method of claim 1, wherein said one or more *Akkermansia muciniphila* strains are administered to a subject identified as having a lower than normal level of *Akkermansia muciniphila* in the gastrointestinal tract.

4. The method of claim 2, wherein said one or more *Akkermansia muciniphila* strains are administered to a subject identified as having a lower than normal level of *Akkermansia muciniphila* in the gastrointestinal tract.

5. The method of claim 3, wherein said subject has severe asthma.

6. The method of claim 1, wherein said one or more *Akkermansia muciniphila* strains are selected from a natu- 9. The method of claim 8, wherein said composition is a beverage or other form of nutritional composition.

10. The method of claim 1, wherein said one or more *Akkermansia muciniphila* strains are in a pharmaceutical composition suitable for delivery of said one or more strains to the gastrointestinal tract.

11. The method of claim 1, wherein said one or more *Akkermansia muciniphila* strains are formulated in a composition which is packaged for aerosol delivery.

12. The method of claim 1, wherein said one or more *Akkermansia muciniphila* strains are administered simultaneously or sequentially with a prebiotic substance suitable for promotion of growth of *Akkermansia muciniphila* in the gastrointestinal tract.

13. The method of claim 1, wherein said one or more *Akkermansia muciniphila* strains are present in a strain-release composition and said method further comprises the pre-step of contacting said composition with a liquid, whereby said one or more strains are released into said liquid and the resulting probiotic liquid composition is ingested.

14. The method of claim 7, wherein the one or more probiotic strains comprise *Lactobacillus* or *Bifidobacterium*.

15. A method for treatment of airway inflammatory activity in a subject having an airway disorder, the method comprising: administration of one or more *Akkermansia*

*muciniphilia* strains to the gastrointestinal tract of a subject having an airway disorder, wherein the airway inflammatory activity of the airway disorder is responsive to increased expression of ILT-4, thereby treating the airway inflammatory activity in the subject.

* * * * *

UNITED STATES PATENT AND TRADEMARK OFFICE
CERTIFICATE OF CORRECTION

Page 1 of 1

PATENT NO. : 10,537,597 B2
APPLICATION NO. : 15/766215
DATED : January 21, 2020
INVENTOR(S) : Liam O'Mahony It is certified that error appears in the above-identified patent and that said Letters Patent is hereby corrected as shown below:

On the Title Page

Item (71) Applicant:
"SCHWEIZERISCHES FORSCHUNGSINSTITUT FUR HOCHGEBRIGSKLIMA UND MEDIZIN IN DAVOS."
Should be replaced with:
— SCHWEIZERISCHES FORSCHUNGSINSTITUT FÜR HOCHGEBIRGSKLIMA UND MEDIZIN IN DAVOS —.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Akkermansia muciniphila-specifc primer sequence
      AM1

<400> SEQUENCE: 1
cagcacgtga aggtg                                                      15

<210> SEQ ID NO 2
<211> LENGTH: 18
<212> TYPE: DNA
<213> ORGANISM: Artificial Sequence
<220> FEATURE:
<223> OTHER INFORMATION: Akkermansia muciniphila-specifc primer sequence
      AM2

<400> SEQUENCE: 2
ccttgcggtt ggcttcag                                                   18
```